(12) United States Patent
Tal et al.

(10) Patent No.: US 11,264,140 B1
(45) Date of Patent: Mar. 1, 2022

(54) SYSTEM AND METHOD FOR AUTOMATED PHARMACEUTICAL RESEARCH UTILIZING CONTEXT WORKSPACES

(71) Applicant: Ro5 Inc., Dallas, TX (US)

(72) Inventors: Roy Tal, Dallas, TX (US); Zygimantas Jocys, Hove (GB); Charles Dazler Knuff, Dallas, TX (US)

(73) Assignee: RO5 INC., Dallas, TX (US)

( * ) Notice: Subject to any disclaimer, the term of this patent is extended or adjusted under 35 U.S.C. 154(b) by 0 days.

(21) Appl. No.: 17/387,859

(22) Filed: Jul. 28, 2021

Related U.S. Application Data

(63) Continuation-in-part of application No. 17/166,435, filed on Feb. 3, 2021, now Pat. No. 11,080,607.

(60) Provisional application No. 63/126,349, filed on Dec. 16, 2020.

(51) Int. Cl.
| | | |
|---|---|---|
| *G06F 17/00* | (2019.01) | |
| *G16H 70/40* | (2018.01) | |
| *G06F 16/2457* | (2019.01) | |
| *G16H 20/10* | (2018.01) | |

(52) U.S. Cl.
CPC ....... *G16H 70/40* (2018.01); *G06F 16/24575* (2019.01); *G16H 20/10* (2018.01)

(58) Field of Classification Search
CPC ... G16H 70/40; G16H 20/10; G06F 16/24575

USPC .................................................. 706/45, 12
See application file for complete search history.

(56) References Cited

U.S. PATENT DOCUMENTS

| | | | |
|---|---|---|---|
| 2015/0235143 A1* | 8/2015 | Eder | G16Z 99/00 706/12 |
| 2016/0063180 A1 | 3/2016 | Weaver et al. | |
| 2019/0303535 A1* | 10/2019 | Fokoue-Nkoutche | G06N 7/005 |
| 2020/0160201 A1 | 5/2020 | Katuwal et al. | |
| 2021/0057050 A1 | 2/2021 | Zavoronkovs et al. | |

* cited by examiner

*Primary Examiner* — Charlotte M Baker
(74) *Attorney, Agent, or Firm* — Galvin Patent Law LLC; Brian R. Galvin

(57) ABSTRACT

A system and method for an automated pharmaceutical research utilizing contextual workspaces comprising a workspace drive engine, a data analysis engine, one or more machine and deep learning modules, a knowledge graph, and a workspace interface, which can create a virtual research workspace where data files containing biochemical data related to current research can be uploaded, which automatically processes and analyzes the uploaded data file to autonomously extract a plurality of information related to the uploaded data file, which performs various similarity searches on the uploaded data, and which formats and displays all the extracted information in the workspace, such that the workspace may provide a deeper contextualized view of the uploaded biochemical data.

8 Claims, 26 Drawing Sheets

SYSTEM AND METHOD FOR AUTOMATED PHARMACEUTICAL RESEARCH UTILIZING CONTEXT WORKSPACES

CROSS-REFERENCE TO RELATED APPLICATIONS

Priority is claimed in the application data sheet to the following patents or patent applications, the entire written description, including figures, of each of which is expressly incorporated herein by reference in its entirety:
Ser. No. 17/166,435
63/126,349

BACKGROUND

Field of the Art

The disclosure relates to the field of bioinformatics, and more particularly to the field of data processing and analysis for mapping relations between biological and chemical unstructured data.

Discussion of the State of the Art

There are a multitude of existing databases that contain medical information. For a given domain, there may even exist a massive amount of databases, siloed from each other, that contain similar information. In particular, the domains related to diseases, genetic information, proteins, molecules, assays, clinical trials, and biological pathways/mechanisms are vital to pharmaceutical research and the large plurality of databases containing information for each of these particular domains provide evidence of their importance. Many of these databases allow a researcher (user) to query and search for information contained within. To collate information about a domain of interest, the researcher must manually locate databases that provide the required and appropriate information, query the database, and extract information from the returned data, not to mention any possible data formatting that may be required when exporting data from the located databases. This process requires a large amount of time and skills that a researcher may not possess. Furthermore, finding links between data domains across multiple databases is a tedious process as there are seemingly no deeper relational networks based on biochemical properties and other calculated, learned, or inferred associations. Additionally, existing systems that implement relational databases often use the relations to assist with the input dataset to train models, and not to supplement the results from those models which can lead to less robust predictions and model output.

Present day bioinformatic resources include a massive amount of databases containing medical, biological, and chemical information that spans decades of research, as well as bioinformatic and cheminformatic tools that help analyze these databases. However, these databases are often siloed away from each other and not augmented with modern machine learning and computational techniques. For example, the sc-PDB (Protein Data Bank) database might contain experimentally annotated binding sites on proteins, but it does not predict new potential binding sites using a variety of methods, nor does it have a robust query for binding site similarity or a bioactivity predictor to screen new molecules against the binding site in silico, nor does it have a De Novo generator to create new molecules within a binding site of interest.

Furthermore, synthesizing existing biomedical information in order to contextualize current, novel research can be a time and labor intensive endeavor. Additionally, it is generally impossible for a user to contextualize all information in an unbiased manner. For instance, if the user discovers a molecule, he or she cannot automatically search through the entire database of similar molecules, using different metrics for similarity and see what are the effects of very similar molecules (e.g., Toxic, active at another receptor, etc.).

What is needed is a system and method for automated pharmaceutical research utilizing context workspaces which combines file management, exploratory drug analysis, machine learning modules, and a knowledge graph to create a secure workspace to understand novel research in the context of existing research (data and literature-derived) and generate new hypotheses.

SUMMARY

Accordingly, the inventor has conceived and reduced to practice, a system and method for an automated pharmaceutical research utilizing context workspaces comprising a workspace drive engine, a data analysis engine, one or more machine and deep learning modules, a knowledge graph, and a workspace interface, which can create a virtual research workspace where data files containing biochemical or medical data related to current research can be uploaded, which automatically processes and analyzes the uploaded data file to autonomously extract a plurality of information related to the uploaded data file, which performs various similarity searches on the uploaded data, and which formats and displays all the extracted information in the workspace, such that the workspace may provide a deeper contextualized view of the uploaded biochemical and biomedical data.

According to a first preferred embodiment, a system for automated pharmaceutical research utilizing context workspaces, is disclosed, comprising: a computer system comprising a memory and a processor; a workspace database, comprising information related to uploaded biochemical and biomedical data files, extracted information, and saved workspace data; a biochemical database, comprising biochemical and biomedical information related to at least, genes, disease, proteins, molecules, drugs, clinical trials, assays, and biological pathways/mechanisms; a workspace drive engine, comprising a first plurality of programming instructions stored in the memory of, and operating on the processor, wherein the first plurality of programming instructions, when operating on the processor, cause the computer system to: create a new workspace; store the created workspace in the workspace database; receive an uploaded data file, the uploaded data file comprising at least one biochemical or biomedical entity; create a copy of the uploaded data file; store the copy of the uploaded data file in the workspace database; parse the uploaded data file into individual biochemical or biomedical entities; determine if the individual biochemical or biomedical entity exists within the biochemical database, wherein a detected biochemical or biomedical entity indicates the individual biochemical or biomedical entity exists in the biochemical database, and an undetected biochemical or biomedical indicates the individual biochemical of biomedical entity does not exist in the biochemical database; send an undetected biochemical or biomedical entity to a data analysis engine; extract all information related to a detected biochemical or biomedical entity from a knowledge graph; create a graph-based representation of the extracted information; receive data related to a decoded vector from a data analysis engine; extract all information related to the decoded vector from the knowledge graph; and format the data related to the decoded vector, the extracted information, and the graph-based representation for display in the workspace; and a data analysis engine, comprising a second plurality of programming instructions stored in the memory of, and operating on the processor, wherein the second plurality of programming instructions, when operating on the processor, cause the computer system to: receive the undetected biochemical or biomedical entity; input the undetected biochemical or biomedical entity into a trained encoder to create an abstract vector representation of the undetected biochemical or biomedical entity, existing in the abstract latent space of a three-dimensional convolutional neural network; compute the distance between two abstract vectors within the latent space; compare the computed distance to a predetermined threshold of similarity, wherein a computed distance less than the threshold indicates non-similarity between the two abstract vectors and a computed distance greater than the threshold indicates similarity; and decode the abstract vector that is greater than the threshold and return to the workspace drive engine data related to the decoded vector as a response to the received undetected biochemical or biomedical entity.

According to another preferred embodiment, a method for automated pharmaceutical research utilizing context workspaces is disclosed, comprising the steps of: creating a new workspace; storing the created workspace in the workspace database; receiving an uploaded data file, the uploaded data file comprising at least one biochemical or biomedical entity; creating a copy of the uploaded data file; storing the copy of the uploaded data file in the workspace database; parsing the uploaded data file into individual biochemical or biomedical entities; determining if the individual biochemical or biomedical entity exists within the biochemical database, wherein a detected biochemical or biomedical entity indicates the individual biochemical or biomedical entity exists in the biochemical database, and an undetected biochemical or biomedical indicates the individual biochemical or biomedical entity does not exist in the biochemical database; sending an undetected biochemical or biomedical entity to a data analysis engine; extracting all information related to a detected biochemical or biomedical entity from a knowledge graph; creating a graph-based representation of the extracted information; receiving data related to a decoded vector from a data analysis engine; extracting all information related to the decoded vector from the knowledge graph; formatting the data related to the decoded vector, the extracted information, and the graph-based representation for display in the workspace; receive the undetected biochemical or biomedical entity; inputting the undetected biochemical or biomedical entity into a trained encoder to create an abstract vector representation of the undetected biochemical or biomedical entity, existing in the abstract latent space of a three-dimensional convolutional neural network; computing the distance between two abstract vectors within the latent space; comparing the computed distance to a predetermined threshold of similarity, wherein a computed distance less than the threshold indicates non-similarity between the two abstract vectors and a computed distance greater than the threshold indicates similarity; and decoding the abstract vector that is greater than the threshold and return to the workspace drive engine data related to the decoded vector as a response to the received undetected biochemical or biomedical entity.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

DETAILED DESCRIPTION

Figure 1:
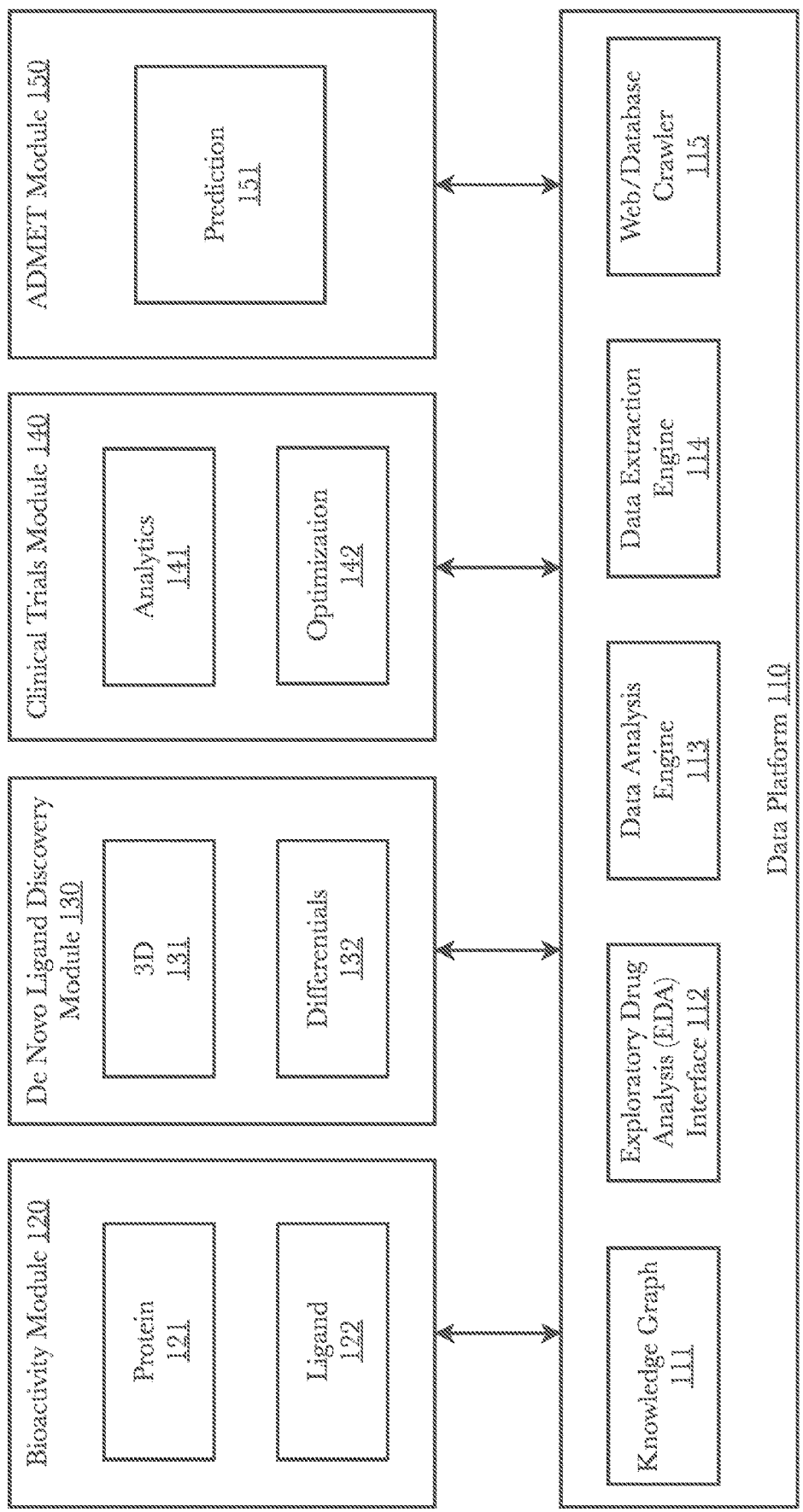
FIG. 1 is a block diagram illustrating an exemplary overall system architecture for a pharmaceutical research system, according to one aspect.

The inventor has conceived, and reduced to practice, a system and method for an automated pharmaceutical research utilizing context workspaces comprising a workspace drive engine, a data analysis engine, one or more machine and deep learning modules, a knowledge graph, and a workspace interface, which can create a virtual research workspace where data files containing biochemical and biomedical data related to current research can be uploaded, which automatically processes and analyzes the uploaded data file to autonomously extract a plurality of information related to the uploaded data file, which performs various similarity searches on the uploaded data, and which formats and displays all the extracted information in the workspace, such that the workspace may provide a deeper contextualized view of the uploaded biochemical and biomedical data.

The custom-built knowledge graph is a massive relational database that maps relations between biological and chemical unstructured data. The knowledge graph may encompass the following features: binding affinity data between proteins and drugs, protein-to-protein data bank binding site similarity search, biological pathways, assay-to-protein relations, molecular similarity search, omics data (e.g., genomics, proteomics, transcriptomics, metabolomics, etc.), protein visualization, homology modeling, historical clinical trial data, as well as all possible data or literature derived and inferred relationships thereof, and enrichment of the data through literature extraction from sources such as research papers, theses, historical clinical trial data, electronic health records, grants, investigational new drug applications (IND), federal drug administration (FDA) documents, chemical and biological patents, and any other biochemical or biomedical text.

The data platform for automated pharmaceutical research ingests a large number of biochemical and biomedical information databases providing information across a broad range of biological and chemical entities. A large plurality of databases related to various data categories including, but not limited to genetic information, drugs, molecules, diseases, biological pathways/mechanisms, and proteins are ingested, processed, and linked to form a large network of chemical and biological data. Databases containing similar data about a data category are mapped to each other before all available data from each data source is collated into one single entry in a data category. These single entries then become nodes in a data category specific knowledge graph.

For example, two ingested data sources provide information about the same data category such as proteins, and furthermore, they contain data about the same list of proteins, although the data provided by each data source for each individual protein may not be uniform. The two protein databases would be mapped to each other under the data category of proteins, and each of the individual proteins in the protein databases would be mapped into the proteins hierarchy, wherein the data from both databases related to the same protein are collated and stored in a proteins database. A protein-specific knowledge graph may be derived using only the proteins database. As a knowledge graph structure this would resemble a large parent node labeled "Proteins" with the individual proteins contained in the two databases as child nodes, wherein a child node contains all available information about a given protein collated into one general repository with links to the original source data via the mapping.

This general structure of the knowledge graph applies to each of the above mentioned data categories. The data platform supports a plurality of data category-specific knowledge graphs that represents a unified repository for information related to the data categories of genetic information, drugs, molecules, biological pathways/mechanisms, and proteins. A category-specific knowledge graph can be thought of as a hybrid dictionary-thesaurus that supports search queries. For example, a researcher may input a molecule into a user interface, and the data platform will retrieve from the molecule knowledge graph all its related information such as, but not limited to its properties such as weight, composition, structure, uses, a common description, assays, target information, and any synonyms that also refer to the input molecule.

The data platform for automated pharmaceutical research also features literature extraction whereby a knowledge graph of data category entries and their relationships is constructed from literature. The data platform automates the work of a human reader who reads abstracts one by one and writes down relationships from a closed list between terms, also from a closed list, as he or she encounters them. In a preferred embodiment, the literature extraction process focuses on the entities of various types including, but not limited to genes, proteins, drugs, biological pathways/mechanisms, and diseases which is supported by internally stored and manually curated lists for each entity type. The knowledge graph derived from literature extraction is comprised of nodes which represent an entity term of a specific type, and edges which represent the relationships between terms. The nodes represent entities that exist in the above mentioned category-specific knowledge graphs. Additional nodes referencing the above mentioned entities may include a PubMed ID and/or the source publication. Source publication nodes can provide context for any relationship pair (linking otherwise invisible entities in the same paper but outside of this pair), explicitly specify scope, and thus allow to query for, reason and accumulate knowledge about k-degree relationships (e.g., sequences), as opposed to strictly 2-degree relationships (e.g., pairs). Ultimately, what this process can do is contextualize any relationship with the publication from which it was derived to reveal more insights. This means that the relationships extracted from the literature connect, as edges, the category-specific knowledge graphs together to form a massive, unified knowledge graph which can support advanced search queries spanning a plurality of data categories. To extract relationships between entity terms, the data platform utilizes natural language processing (NLP) algorithms and a plurality of verb databases specific to each entity type. The verb databases are compiled using available existing medical terminology as well as manual curation from domain experts.

According to an embodiment, an automated pharmaceutical research utilizing context workspaces system may integrate with the data platform and its subcomponents. A workspace drive engine may be integrated with the data platform to automatically provide researchers with a large plurality of context data, derived from the custom-built knowledge graph and extracted literature information, in order to better understand their current research in relation to existing and inferred biochemical and biomedical data. For example, a researcher may create a virtual research workspace where she can upload a data file containing information about some research she is currently conducting, and the workspace drive engine can automatically process and analyze the information on the uploaded data file to detect if any of the information currently exists on the data platform. Existing, detected information may have all the information related to it extracted from the knowledge graph and returned to the workspace so that the researcher may view and interact with the data. Such interactions may include graph-based tools that allow the researcher to understand the extracted information better. Additionally, the workspace drive engine may integrate with one or more machine learning models to generate predictions and inferred data related to a researcher's uploaded data file. Context workspaces may be stored in a database located within the data platform and accessible at any time via logging into the workspace user interface.

The global pandemic public health emergency known as coronavirus disease 2019 (COVID-19) has caused deaths worldwide and led to social and economic disruption. A global pandemic fueled a collaborative, global effort to gain as much information about SARS-CoV-2 and how to combat it. In early January of 2020 Chinese authorities shared the full sequence of the SARS-CoV-2 genome which was a crucial first step for the development of specific diagnostic tests and identification of potential options. If the disclosed automated pharmaceutical research system had existed in January when the genomic sequence of SARS-CoV-2 was released, it would have massively aided in solving the COVID-19 problem. For instance, the COVID-19 genome sequence could have been input into the automated pharmaceutical research data platform which would then search for similar proteins using a comprehensive similarity search routine and identify the severe acute respiratory syndrome coronavirus 2 (SARS-CoV-2) spike protein as similar based on genome sequence data. There is a large amount of data available about SARS-CoV-1 because it has triggered dangerous epidemics in the past and is well studied, and this data has been ingested and integrated into the automated pharmaceutical research data platform. For example, it has been published that SARS-CoV-1 uses the angiotensin-converting enzyme 2 (ACE2) as the entry receptor. This prior information and the mechanisms involved from the previous coronavirus, SARS-CoV-1, could have been used to understand the mechanism of SARS-CoV-2 and how to potentially create drugs against it. This latter part could be done with the Bioactivity module, where once targets are identified (in this case human targets, based on mechanism of action of the virus), they could be inputted into the Bioactivity module to test existing drugs for repurposing. This same process could be accomplished using a 3-D Bioactivity model or also generate novel compounds completely using De Novo module. Using these processes, the platform could also identify potential targets for the inhibition of SARS-CoV-2, including important viral proteins necessary for its replication process. Additionally, the system may return all information related to the identified protein receptors including information extracted from assays and clinical trials. This information may include data about potential treatments or drugs related to the identified proteins that may be used to treat COVID-19. In this way the data platform for automated pharmaceutical research may have provided a solution to the COVID-19 problem had the system existed in January of 2020.

The data platform for automated pharmaceutical research supports a plurality of modules that further enhance the research capabilities of the system. The bioactivity module utilizes the data platform to analyze and predict the bioactivity of molecules based on protein and ligand similarities and known or suspected protein and ligand compatibilities. The module utilizes the knowledge graph and data analysis engine capabilities of the data platform, and in one embodiment is configured to predict the bioactivity of a molecule based on and their known or suspected compatibilities with certain combinations of proteins and ligands. Thus, using the bioactivity module, users can research molecules by entering queries through the EDA interface, and obtaining predictions of bioactivity based on known or suspected bioactivity of similar molecules and their compatibilities with certain protein and ligand combinations.

The Bioactivity machine learning model may be trained to predict the inhibitory activity level between a small molecule and a target protein. The model is designed to learn from graph representations of molecules by generating a vector to capture their chemical structure and reactivity. When combined with a protein representation derived from sequence information alone, the model produces a bioactivity prediction for the pair. Additionally, the Bioactivity model may use 3D information of both the molecule and the protein's binding pocket to produce a bioactivity prediction. The data platform for automated pharmaceutical research may evaluate all combinations of compounds and target proteins. The results may be filtered based on desired activity level and, furthermore, the molecules may be ranked by their probability of inhibiting a specified protein process. The filtered and ranked results are assessed according to their chemical and pharmacological relevance using the data stored within the data platform. The end result is a list of several identified compounds highly likely to be inhibitors. This list of compounds may be used by researchers and further tested in a preclinical setting to investigate the efficacy of the listed compounds in combating a disease through inhibitory processes.

The de novo ligand discovery module utilizes the data platform to identify ligands and their properties through data enrichment and interpolation/perturbation. The module utilizes the knowledge graph and data analysis engine capabilities of the data platform, and in one embodiment is configured to identify ligands with certain properties based on three dimensional (3D) models of known ligands and differentials of atom positions in the latent space of the models after encoding by a 3D convolutional neural network (3D CNN), which is part of the data analysis engine. In one embodiment, the 3D model comprises a voxel image (volumetric, three dimensional pixel image) of the ligand. In cases where enrichment data is available, ligands may be identified by enriching the SMILES string for a ligand with information about possible atom configurations of the ligand and converting the enriched information into a plurality of 3D models of the atom. In cases where insufficient enrichment information is available, one possible configuration of the atoms of the ligand may be selected, and other configurations may be generated by interpolation or perturbation of the original configuration in the latent space after processing the 3D model through the CNN. In either case, the 3D models of the ligands are processed through a CNN, and a gradient descent is applied to changes in atom configuration in the latent space to identify new ligands with properties similar to the modeled ligands. Thus, using the de novo ligand discovery module, users can identify new ligands with properties similar to those of modeled ligands by entering queries through the EDA interface.

The de novo ligand discovery module may further comprise a 3D based de novo which can take the protein binding site structure into account, which can also be either extracted directly form the knowledge graph or can use a machine learned binding site identified by the data platform. This can then be fed into a pocket-based 3D de novo model to generate novel compounds that are specifically optimized for bioactivity and other chemical and pharmacological properties.

An important component of pharmaceutical research is identifying and characterizing the disposition of a compound within an organism. The ADMET module utilizes the data platform to discover and predict absorption, distribution, metabolism, excretion, and toxicity characteristics of ligands based on ADMET databases. The module utilizes the knowledge graph and data analysis engine capabilities of the data platform, and in one embodiment is configured to return ligands with characteristics similar to, or dissimilar to, a specified ligand in one or more respects (e.g., a ligand with similar absorption and metabolism characteristics, but dissimilar toxicity characteristics) based on semantic clustering within the knowledge graph. Furthermore, the module may extract ADMET substructures from the knowledge graph. Thus, using the ADMET module, users can research a large ADMET database based on aspects of interest by entering queries through the EDA interface.

The clinical trials module utilizes the data platform to analyze and optimize the knowledge contained in or derived from clinical trials. The module utilizes the knowledge graph and data analysis engine capabilities of the data platform, and in one embodiment is configured to return clinical trials similar to a specified clinical trial in one or more aspects (e.g., proteins and ligands studied, methodology, results, etc.) based on semantic clustering within the knowledge graph. Thus, using the clinical trials module, users can research a large database of clinical trials based on aspects of interest by entering queries through the EDA interface.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Definitions

"Bioactivity" as used herein means the physiological effects of a molecule on an organism, including but not limited to effects on substructures, organs, cells, proteins, or metabolic pathways of the organism.

"Edges" and "Relationships" as used herein interchangeably means connections between nodes or vertices in a data structure. In graphs, an arbitrary number of edges may be assigned to any node or vertex, each edge representing a relationship to itself or any other node or vertex. Edges may also include properties such as value, conditions, or other information, such as edge weights or probabilities.

"FASTA" as used herein means any version of the FASTA family (e.g., FASTA, FASTP, FASTA, etc.) of chemical notations for describing nucleotide sequences or amino acid (protein) sequences using text (e.g., ASCII) strings.

"Ligand" as used herein means a substance that forms a complex with a biomolecule to serve a biological purpose. In protein-ligand binding, the ligand is usually a molecule which produces a signal by binding to a site on a target protein. Ligand binding to a receptor protein alters the conformation by affecting the three-dimensional shape orientation. The conformation of a receptor protein composes the functional state. Ligands comprise substrates, inhibitors, activators, signaling lipids, and neurotransmitters.

"Nodes", "Vertices", and "Entities" are used herein interchangeably to mean a unit of a data structure comprising a value, condition, or other information. Nodes and vertices may be arranged in lists, trees, graphs, and other forms of data structures. In graphs, nodes and vertices may be connected to other nodes via an arbitrary number of edges, which represent relationships between the nodes or vertices. As the context requires, the term "node" may also refer to a node of a neural network (also referred to as a neuron) which is analogous to a graph node in that it is a point of information connected to other points of information through edges.

"Proteins" as used herein means large biomolecules, or macromolecules, consisting of one or more long chains of amino acid residues. Proteins perform a vast array of functions within organisms, including catalyzing metabolic reactions, DNA replication, responding to stimuli, providing structure to cells and organisms, and transporting molecules from one location to another. Proteins differ from one another primarily in their sequence of amino acids, which is dictated by the nucleotide sequence of their genes, and which usually results in protein folding into a specific 3D structure that determines its activity.

"SMILES" as used herein means any version of the "simplified molecular-input line-entry system," which is a form of chemical notation for describing the structure of molecules using short text (e.g., ASCII) strings.

Conceptual Architecture

FIG. 1 is a block diagram illustrating an exemplary overall system architecture for a pharmaceutical research system. The exemplary architecture comprises a data platform 110 which provides the core functionality of the system, plus one or more modules that utilize the data platform 110 to provide functionality in specific areas of research, in this case a bioactivity module 120, a de novo ligand discovery module 130, a clinical trials module 140, and an absorption, distribution, metabolism, excretion, and toxicity (ADMET) module 150.

The data platform 110 in this embodiment comprises a knowledge graph 111, an exploratory drug analysis (EDA) interface 112, a data analysis engine 113, a data extraction engine 114, and web crawler/database crawler 115. The crawler 115 searches for and retrieves medical information such as published medical literature, clinical trials, dissertations, conference papers, and databases of known pharmaceuticals and their effects. The crawler 115 feeds the medical information to a data extraction engine 114, which uses natural language processing techniques to extract and classify information contained in the medical literature such as indications of which molecules interact with which proteins and what physiological effects have been observed. Using the data extracted by the data extraction engine 114, a knowledge graph 111 is constructed comprising vertices (also called nodes) representing pieces of knowledge gleaned from the data and edges representing relationships between those pieces of knowledge. As a very brief example, it may be that one journal article suggests that a particular molecule is useful in treating a given disease, and another journal article suggests that a different molecule is useful for treating the same disease. The two molecules and the disease may be represented as vertices in the graph, and the relationships among them may be represented as edges between the vertices. The EDA interface 112 is a user interface through which pharmaceutical research may be performed by making queries and receiving responses. The queries are sent to a data analysis engine 113 which uses the knowledge graph 111 to determine a response, which is then provided to the user through the EDA interface 112. In some embodiments, the data analysis engine 113 comprises one or more graph-based neural networks (graph neural networks, or GNNs) to process the information contained in the knowledge graph 111 to determine a response to the user's query. As an example, the user may submit a query for identification of molecules likely to have similar bioactivity to a molecule with known bioactivity. The data analysis engine 113 may process the knowledge graph 111 through a GNN to identify such molecules based on the information and relationships in the knowledge graph 111.

The bioactivity module 120 utilizes the data platform 110 to analyze and predict the bioactivity of molecules based on protein 121 and ligand 122 similarities and known or suspected protein 121 and ligand 122 compatibilities. The module utilizes the knowledge graph 111 and data analysis engine 113 capabilities of the data platform 110, and in one embodiment is configured to predict the bioactivity of a molecule based on and their known or suspected compatibilities with certain combinations of proteins 121 and ligands 122. Thus, using the bioactivity module 120, users can research molecules by entering queries through the EDA interface 112, and obtaining using predictions of bioactivity based on known or suspected bioactivity of similar molecules and their compatibilities with certain protein 121 and ligand 122 combinations.

The de novo ligand discovery module 130 utilizes the data platform 110 to identify ligands and their properties through data enrichment and interpolation/perturbation. The module utilizes the knowledge graph 111 and data analysis engine 113 capabilities of the data platform 110, and in one embodiment is configured to identify ligands with certain properties based on three dimensional (3D) models 131 of known ligands and differentials of atom positions 132 in the latent space of the models after encoding by a 3D convolutional neural network (3D CNN), which is part of the data analysis engine 113. In one embodiment, the 3D model comprises a 3D model (three-dimensional image made of voxels) of the molecules. In cases where enrichment data is available, ligands may be identified by enriching the SMILES string for a ligand with information about possible atom configurations of the ligand and converting the enriched information into a plurality of 3D models of the atom. In cases where insufficient enrichment information is available, one possible configuration of the atoms of the ligand may be selected, and other configurations may be generated by interpolation or perturbation of the original configuration in the latent space after processing the 3D model through the CNN. In either case, the 3D models of the ligands are processed through a CNN, and a gradient descent is applied to changes in atom configuration in the latent space to identify new ligands with properties similar to the modeled ligands. Thus, using the de novo ligand discovery module 130, users can identify new ligands with properties similar to those of modeled ligands by entering queries through the EDA interface 112.

The clinical trials module 140 utilizes the data platform 110 to analyze 141 and optimize 142 the knowledge contained in or derived from clinical trials. The module utilizes the knowledge graph 111 and data analysis engine 113 capabilities of the data platform 110, and in one embodiment is configured to return clinical trials similar to a specified clinical trial in one or more aspects (e.g., proteins and ligands studied, methodology, results, etc.) based on semantic clustering within the knowledge graph 111. Thus, using the clinical trials module 140, users can research a large database of clinical trials based on aspects of interest by entering queries through the EDA interface 112.

The ADMET module 150 utilizes the data platform 110 to discover 151 and predict 152 absorption, distribution, metabolism, excretion, and toxicity characteristics of ligands based on ADMET databases. The module utilizes the knowledge graph 111 and data analysis engine 113 capabilities of the data platform 110, and in one embodiment is configured to return ligands with characteristics similar to, or dissimilar to, a specified ligand in one or more respects (e.g., a ligand with similar absorption and metabolism characteristics, but dissimilar toxicity characteristics) based on semantic clustering within the knowledge graph 111. Thus, using the ADMET module 150, users can research a large ADMET database based on aspects of interest by entering queries through the EDA interface 112.

Figure 2:
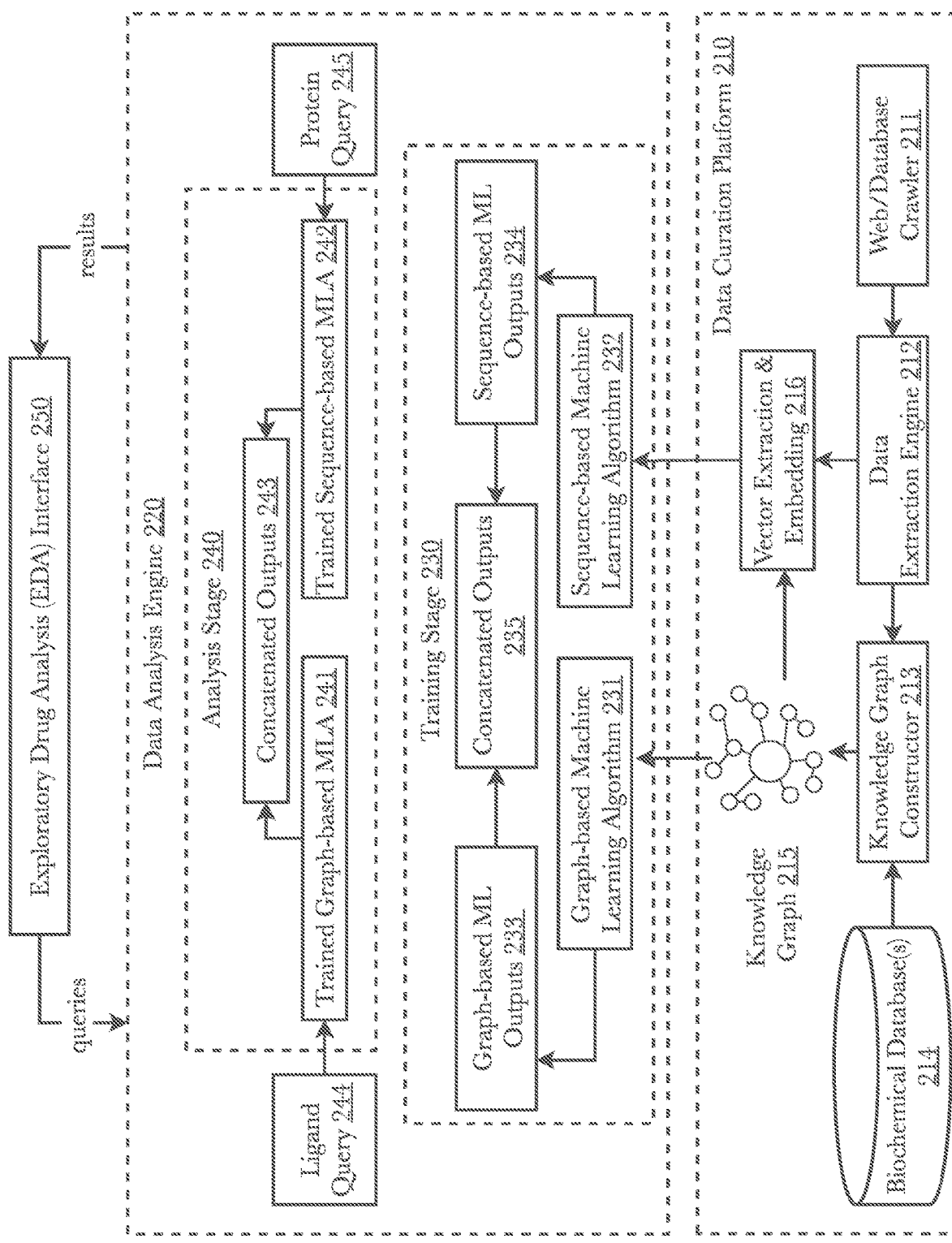
FIG. 2 is a block diagram illustrating an exemplary system architecture for an embodiment of a pharmaceutical research system utilizing combined graph-based and vector-based prediction of molecule bioactivity.

FIG. 2 is a block diagram illustrating an exemplary system architecture for an embodiment of a pharmaceutical research system utilizing combined graph-based and sequence-based prediction of molecule bioactivity. In this embodiment, the system comprises a data curation platform 210, a data analysis engine 220 comprising a training stage 230 and an analysis stage 240, and an exploratory drug analysis interface 250.

In the data curation platform 210, a web crawler/database crawler 211 is configured to search for and download medical information materials including, but not limited to, archives of published medical literature such as MEDLINE and PubMed, archives of clinical trial databases such as the U.S. National Library of Medicine's ClinicalTrials.gov database and the World Health Organization International Clinical Trials Registry Platform (ICTRP), archives of published dissertations and theses such as the Networked Digital Library of These and Dissertations (NDLTD), archives of grey literature such as the Grey Literature Report, and news reports, conference papers, and individual journals. As the medical information is downloaded, it is fed to a data extraction engine 212 which may perform a series of operations to extract data from the medical information materials. For example, the data extraction engine 212 may first determine a format of each of the materials received (e.g., text, PDFs, images), and perform conversions of materials not in a machine-readable or extractable format (e.g., performing optical character recognition (OCR) on PDFs and images to extract any text contained therein). Once the text has been extracted from the materials, natural language processing (NLP) techniques may be used to extract useful information from the materials for use in analysis by machine learning algorithms. For example, semantic analysis may be performed on the text to determine a context of each piece of medical information material such as the field of research, the particular pharmaceuticals studied, results of the study, etc. Of particular importance is recognition of standardized biochemistry naming conventions including, but not limited to, stock nomenclature, International Union of Pure and Applied Chemistry (IUPAC) conventions, and simplified molecular-input line-entry system (SMILES) and FASTA text-based molecule representations. The data extraction engine 212 feeds the extracted data to a knowledge graph constructor 213, which constructs a knowledge graph 215 based on the information in the data, representing informational entities (e.g., proteins, molecules, diseases, study results, people) as vertices of a graph and relationships between the entities as edges of the graph. Biochemical databases 214 or similar sources of information may be used to supplement the graph with known properties of proteins, molecules, physiological effects, etc. Separately from the knowledge graph 215, vector representations of proteins, molecules, interactions, and other information may be represented as vectors 216, which may either be extracted from the knowledge graph 215 or may be created directly from data received from the data extraction engine 212.

The data analysis engine 220 utilizes the information gathered, organized, and stored in the data curation platform 210 to train machine learning algorithms at a training stage 230 and conduct analyses in response to queries and return results based on the analyses at an analysis stage 240. In this embodiment, the data analysis engine 220 comprises a dual analysis system which combines the outputs of a trained graph-based machine learning algorithm 241 with the outputs of a trained sequence-based machine learning algorithm 242. The trained graph-based machine learning algorithm 241 may be any type of algorithm configured to analyze graph-based data, such as graph traversal algorithms, clustering algorithms, or graph neural networks.

At the training stage 230, information from the knowledge graph 215 is extracted to provide training data in the form of graph-based representations of molecules and the known or suspected bioactivity of those molecules with certain proteins. The graph-based representations of the molecules and their associated bioactivities are used as training input data to a graph-based machine learning algorithm 231, resulting in a graph-based machine learning output 233 comprising vector representations of the characteristics of molecules and their bioactivities with certain proteins. Simultaneously, a sequence-based machine learning algorithm is likewise trained, but using information extracted 216 from the knowledge graph 215 in the form of vector representations of protein segments and the known or suspected bioactivity of those protein segments with certain molecules. The vector representations of the protein segments and their associated bioactivities are used as training input data to a sequence-based machine learning algorithm 232, resulting in a vector-based machine learning output 234 comprising vector representations of the characteristics of protein segments and their bioactivities with certain molecules. In this embodiment, the graph-based machine learning outputs 233 and the sequence-based machine learning outputs 234 are concatenated to produce a concatenated output 235, which serves to strengthen the learning information from each of the separate machine learning algorithms. In some embodiments, the concatenated output may be used to re-train both machine learning algorithms 233, 234 to further refine the predictive abilities of the algorithms.

At the analysis stage, a query in the form of a target ligand 244 and a target protein 245 are entered using an exploratory drug analysis (EDA) interface 250. The target ligand 244 is processed through the trained graph-based machine learning algorithm 241 which, based on its training, produces an output comprising a vector representation of the likelihood of interaction of the target ligand 244 with certain proteins and the likelihood of the bioactivity resulting from the interactions. Similarly, the target protein 245 is processed through the trained sequence-based machine learning algorithm 242 which, based on its training, produces an output comprising a vector representation of the likelihood of interaction of the target protein 245 with certain ligands and the likelihood of the bioactivity resulting from the interactions. The results may be concatenated 243 to strengthen the likelihood information from each of the separate trained machine learning algorithms 241, 242.

Figure 3:
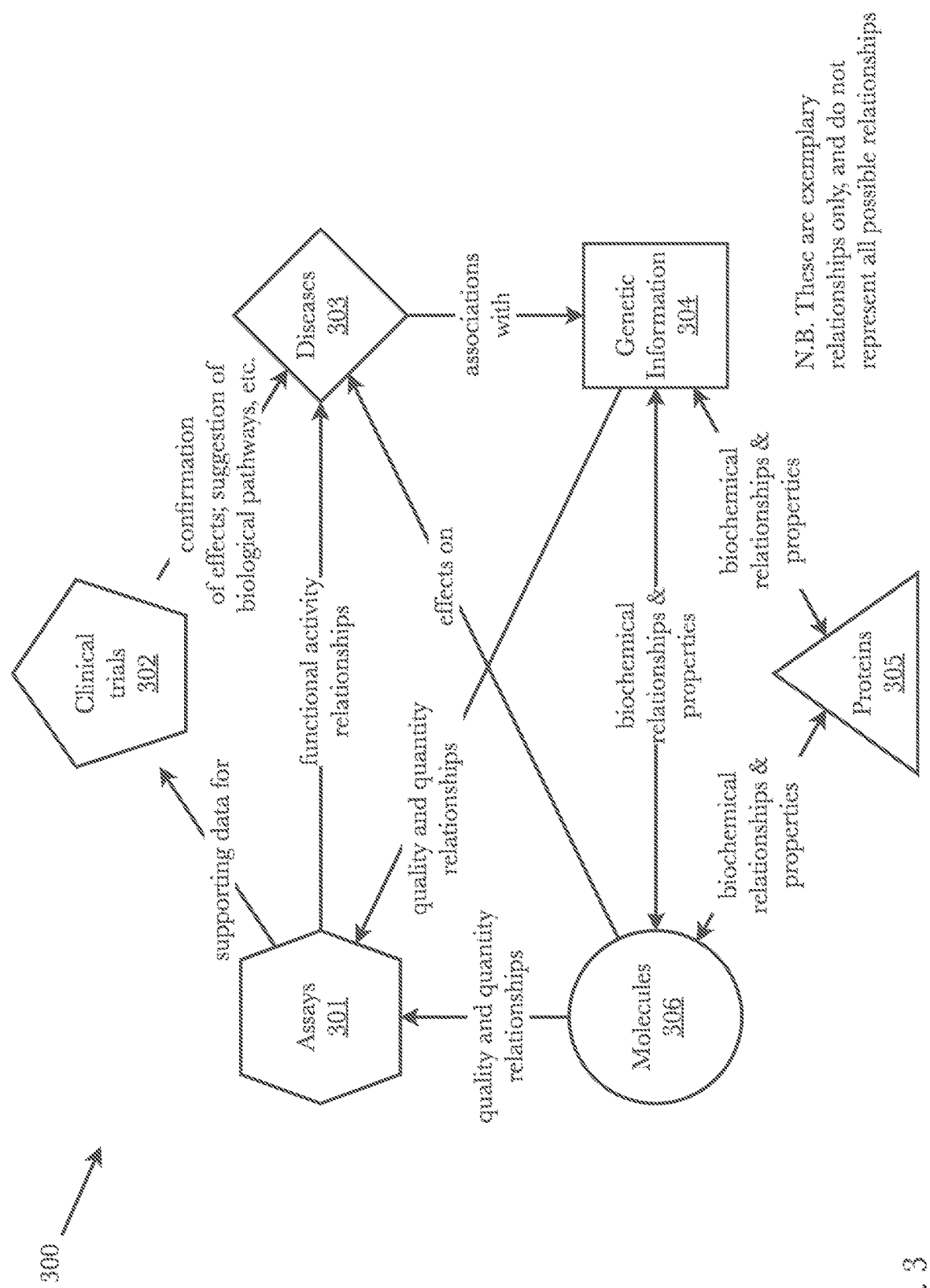
FIG. 3 is a relational diagram illustrating several types of information that may be included in a knowledge graph for a pharmaceutical research system and exemplary relations between those types of information.

FIG. 3 is a relational diagram 300 illustrating several types of information that may be included in a knowledge graph for a pharmaceutical research system and exemplary relations between those types of information. In this example, six types of information are shown with indications of certain relevant relationships and interactions that may be represented in a knowledge graph containing these types of information. The six types of information in this example are chosen to be of particular relevance to pharmaceutical research, and in particular to the analysis of, and prediction of, biochemical and biomedical properties of proteins and ligands as they relate to disease. Proteins 305 and molecules (ligands) 306 are the primary types of information, as their biochemical and biomedical relationships and properties determine effects on diseases 303. Genetic information 304 will have an influence on the production of specific proteins 305 and the association with certain diseases 303. Assays 301 will provide information about the quality and quantity relationships of proteins 350 and molecules 306, which provides supporting data for clinical trials 302 and for functional activity relationships with certain diseases 303. Clinical trials 302 provide confirmation of physiological effects and suggestion of biological pathways related to diseases. While this simplified diagram does not purport to show all types of data that may be included or all relationships that may be relevant, it does show certain important types of data and major relevancies that may be included in a knowledge graph to be used for a pharmaceutical research system.

Figure 4:
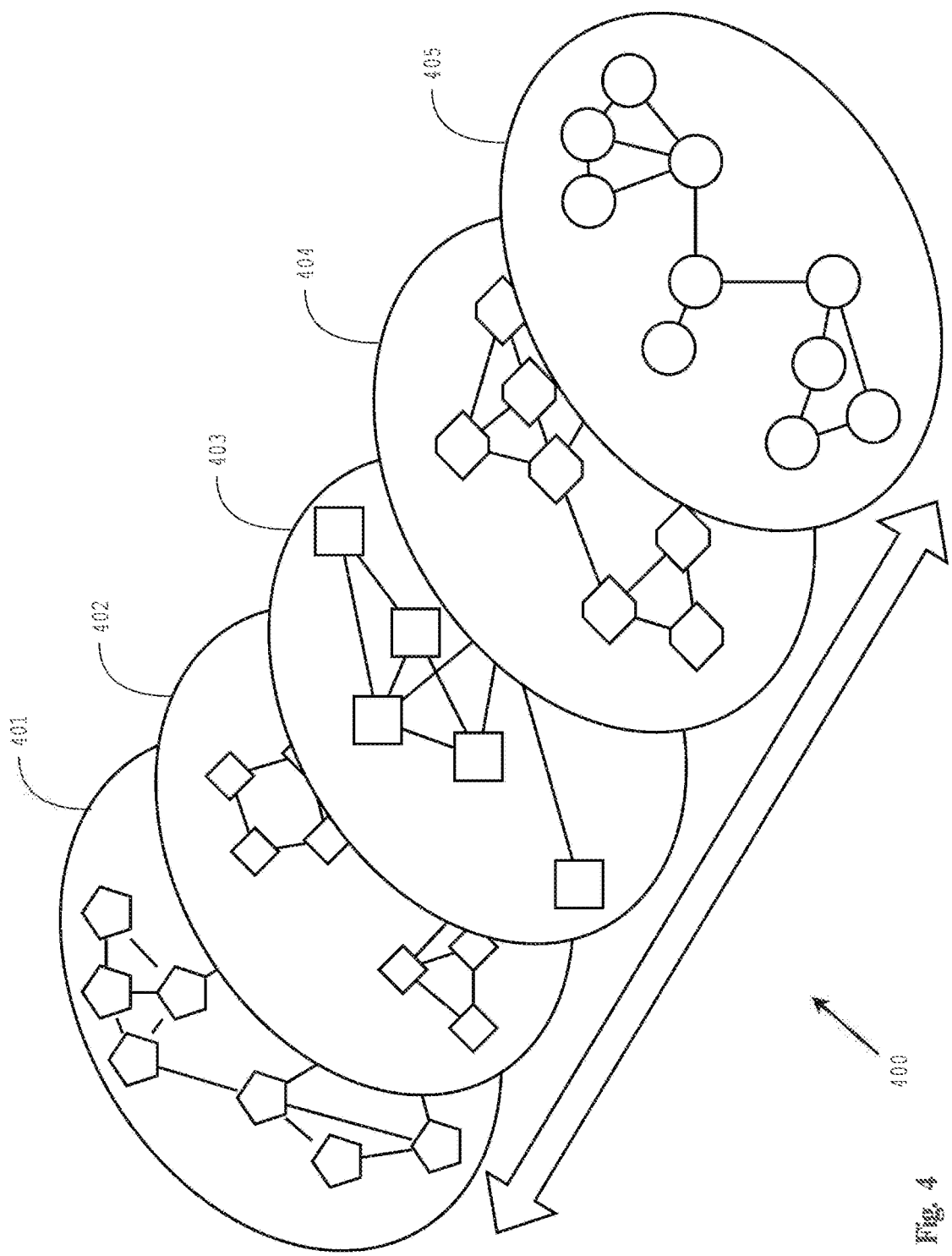
FIG. 4 is a diagram illustrating the conceptual layering of different types of information in a knowledge graph.

FIG. 4 is a diagram illustrating the conceptual layering 400 of different types of information in a knowledge graph. While knowledge graphs are not necessarily constructed in layers, each type of information included in a knowledge graph may be conceived as a layer of information in the knowledge graph and each layer may be analyzed to determine clustering and other relationships within the layer. For example, proceeding with the types of information shown in FIG. 3, the knowledge graph can be conceived of as having layers for clinical trials 401, diseases 402, genetic information 403, assays 404, molecules 405, etc. Relationships such as clustering can be seen at each layer, and can be analyzed separately, if necessary. However, in a knowledge graph, connections between the information at each layer are made and relationships between the information at each layer can be analyzed.

Figure 5:
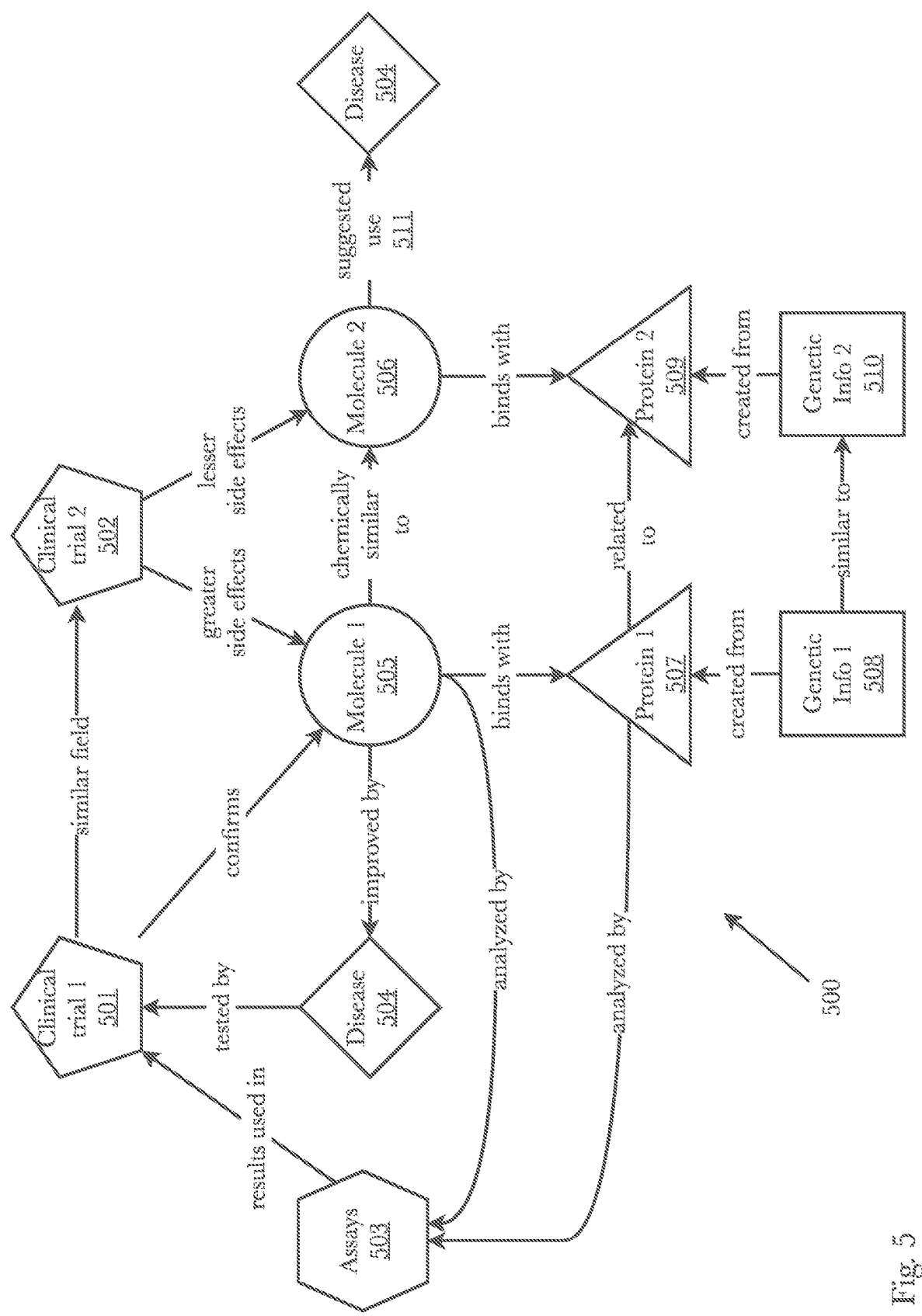
FIG. 5 is a relational diagram illustrating the use of a knowledge graph to predict usefulness of a molecule in treating a disease.

FIG. 5 is a relational diagram illustrating the use of a knowledge graph to predict usefulness of a molecule in treating a disease 500. In this example, a first molecule 505 is known to bind with a first protein 507 which is produced from a first set of genetic information 508. A clinical trial 501 confirmed that the first molecule 505 is effective in treating a disease 504. The clinical trial 501 used information from assays 503 that were performed on the first molecule 505 and the first protein 507. A query has been submitted to the system to identify a second molecule 506 that may also be effective in treating 511 the same disease 504, but with fewer side effects. Using a knowledge graph containing the types of information shown in FIG. 3, and a graph-based machine learning algorithm, the system identifies a second molecule 506 that binds with a second protein 509 which is produced from a second set of genetic information 510. The system determines a number of similarities and relationships between the first molecule 505 and the second molecule 506, including that the first molecule 505 is chemically similar to the second molecule 506, the protein 507 with which the first molecule 505 binds is related to the second protein 509 with which the second molecule 506 binds, and the genetic information (DNA strands) 508 that produces the first protein 507 are similar to the genetic information 510 that produces the second protein 509. Thus, the system determines that the second molecule 506 is likely to have a similar effect on the disease 504 as the first molecule 505. Further, the system identifies a second clinical trial 502 that suggests that the second molecule 506 has lesser side effects than the first molecule 505. As the second molecule 506 meets the query criteria, it is returned as a response to the query.

Figure 6:
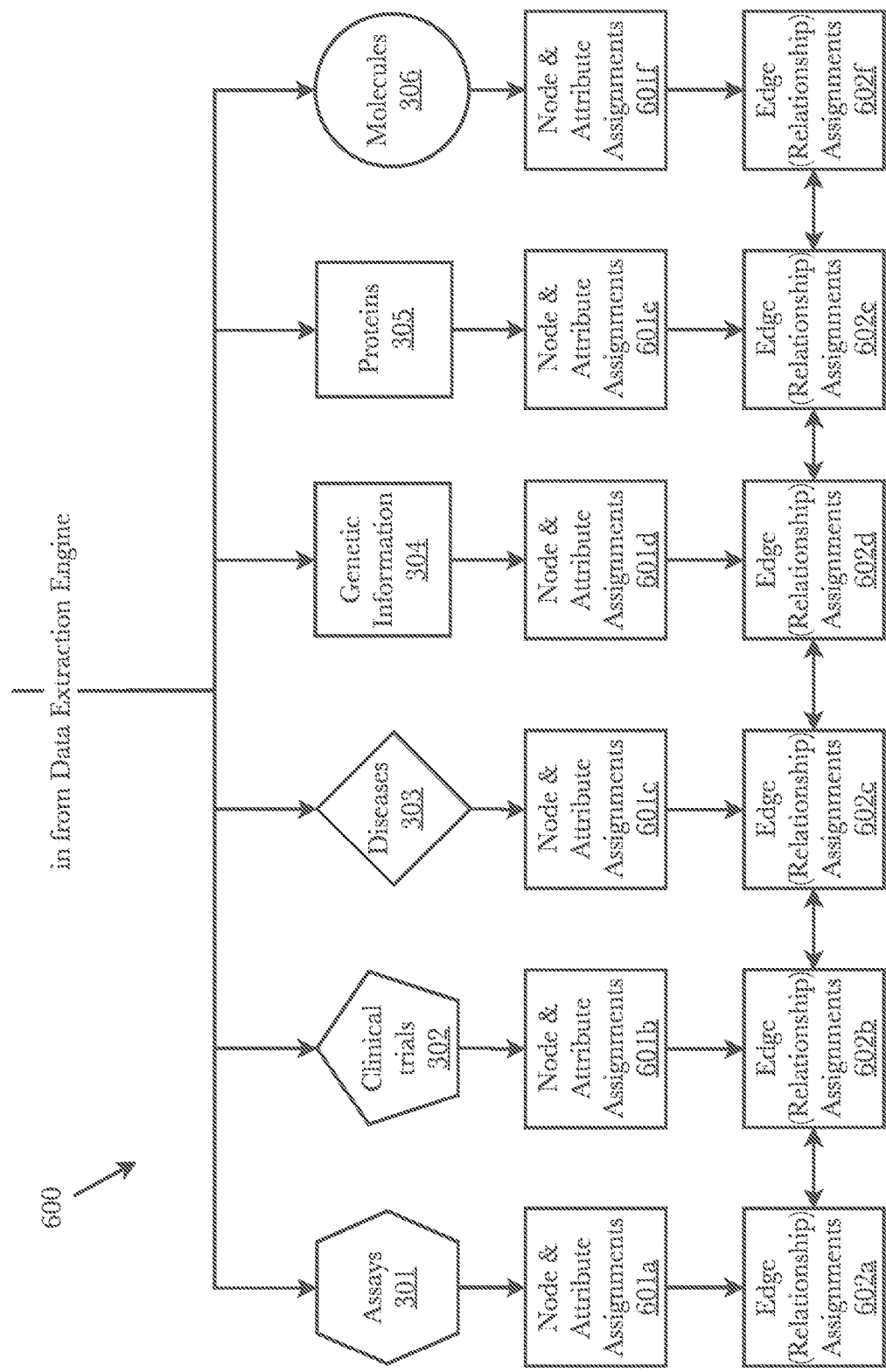
FIG. 6 is a diagram illustrating an exemplary process for combining various types of information into a knowledge graph suitable for a pharmaceutical research system.

FIG. 6 is a diagram illustrating an exemplary process 600 for combining various types of information into a knowledge graph suitable for a pharmaceutical research system. As data is received from a data extraction engine in each of several categories of data (in this example, six categories: assays 301, clinical trials 302, diseases 303, genetic information 304, proteins 305, and molecules 306) nodes are assigned to each entity identified in each category and attributes of the entity are assigned to the node 601a-f. Attributes of the nodes/entity are information describing the characteristics of the nodes/entity. For example, in some embodiments, attributes of nodes related to molecules are in the form of an adjacency matrix which represents the molecule as relationships between the atoms of the molecule. After nodes have been assigned to all identified entities 601a-f, the relationships between entities are assigned, both within the category of knowledge and between all other categories of knowledge 602a-f. As a simple example of the process, assume that a certain molecule 306 is identified during data extraction. A node is created for the molecule and attributes are assigned to the molecule/node in the form of an adjacency matrix representing the molecule as a series of relationships between the atoms of the molecule. Through a series of assays 301 and clinical studies 302, it is known that the molecule binds with a particular protein 305, and is effective in treating a certain disease 303, to which individuals with certain genetic information 304 are susceptible. Nodes are assigned to each of the assays 301, clinical trials 302, diseases 303, proteins 305, and genetic information 304 identified as being associated with the molecule, and edges are established between the nodes reflecting the relevant relationships such as: the molecule binds with the protein, the genetic information is associated with the disease, the clinical trials indicate that the disease is treatable by the molecule, and so on.

Figure 7:
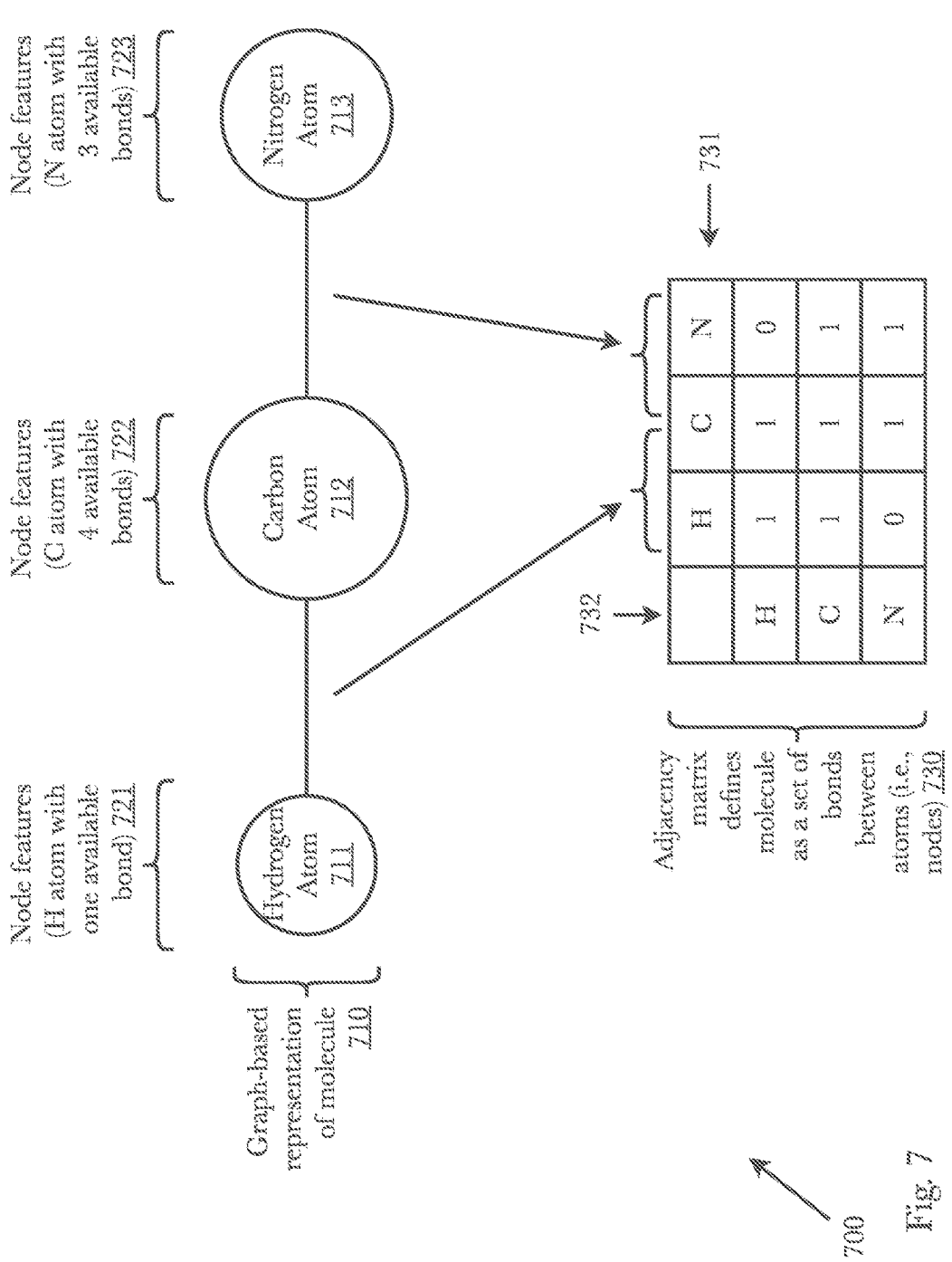
FIG. 7 is a diagram illustrating an exemplary graph-based representation of molecules as simple relationships between atoms using a matrix of adjacencies.

FIG. 7 is a diagram illustrating an exemplary graph-based representation of molecules as simple relationships between atoms using a matrix of adjacencies 700, wherein atoms are represented as nodes and bonds between the atoms are represented as edges. Representation of molecules as a graph is useful because it provides a of molecular structure which can be processed by graph-based machine learning algorithms like GNNs. Further, the graph-based representation of a molecule can be stated in terms of two matrices, one for the node features (e.g., type of atom and its available bonds) and one for the edges (i.e., the bonds between the atoms). The combination of the nodes (atoms) and edges (bonds) represents the molecule.

In this example, a simple hydrogen cyanide molecule is shown as a graph-based representation 710. A hydrogen cyanide molecule consists of three atoms, a hydrogen atom 711, a carbon atom 712, and a nitrogen atom 713. Its standard chemical formula is HCN. Each atom in the molecule is shown as a node of a graph. The hydrogen atom 711 is represented as a node with node features 721 comprising the atom type (hydrogen) and the number of bonds available (one). The carbon atom 712 is represented as a node with node features 722 comprising the atom type (carbon) and the number of bonds available (four). The nitrogen atom 713 is represented as a node with node features 723 comprising the atom type (nitrogen) and the number of bonds available (three). The node features 721, 722, 723 may each be stated in the form of a matrix.

The relationships between the atoms in the molecule are defined by the adjacency matrix 730. The top row of the adjacency matrix 731 shows all of the atoms in the molecule, and the left column of the matrix 732 shows a list of all possible atoms that can be represented by the matrix for a given set of molecules. In this example, the top row 731 and left column 732 contain the same list of atoms, but in cases where multiple molecules are being represented in the system, the left column may contain other atoms not contained in the particular molecule being represented. The matrix shows, for example, that the hydrogen atom 711 is connected to the carbon atom 712 (a "1" at the intersection of the rows and columns for H and C) and that the carbon atom 712 is connected to the nitrogen atom 713 (a "1" at the intersection of the rows and columns for C and N). In this example, each atom is also self-referenced (a "1" at the intersection of the rows and columns for H and H, C and C, and N and N), but in some embodiments, the self-referencing may be eliminated. In some embodiments, the rows and columns may be transposed (not relevant where the matrix is symmetrical, but relevant where it is not).

Figure 8:
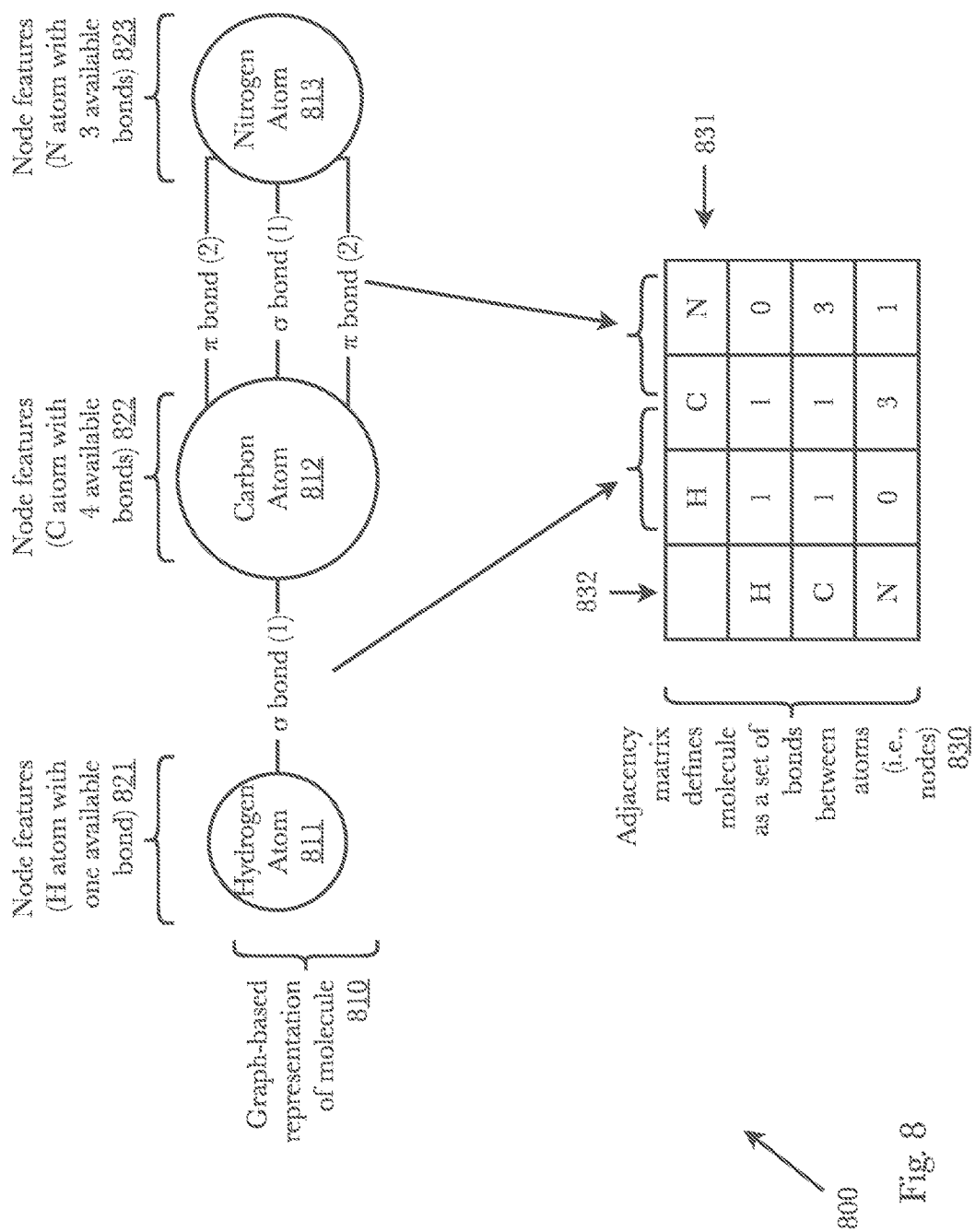
FIG. 8 is a diagram illustrating an exemplary graph-based representation of molecules as relationships between atoms using a matrix of adjacencies wherein the type bonds are distinguished.

FIG. 8 is a diagram illustrating an exemplary graph-based representation of molecules as relationships between atoms using a matrix of adjacencies 800, wherein atoms are represented as nodes and bonds between the atoms are represented as edges, and wherein the type and number of bonds are distinguished. Representation of molecules as a graph is useful because it provides a of molecular structure which can be processed by graph-based machine learning algorithms like GNNs. Further, the graph-based representation of a molecule can be stated in terms of two matrices, one for the node features (e.g., type of atom and its available bonds) and one for the edges (i.e., the bonds between the atoms). The combination of the nodes (atoms) and edges (bonds) represents the molecule.

In this example, a simple hydrogen cyanide molecule is shown as a graph-based representation 810. A hydrogen cyanide molecule consists of three atoms, a hydrogen atom 811, a carbon atom 812, and a nitrogen atom 813. Its standard chemical formula is HCN. Each atom in the molecule is shown as a node of a graph. The hydrogen atom 811 is represented as a node with node features 821 comprising the atom type (hydrogen) and the number of bonds available (one). The carbon atom 812 is represented as a node with node features 822 comprising the atom type (carbon) and the number of bonds available (four). The nitrogen atom 813 is represented as a node with node features 823 comprising the atom type (nitrogen) and the number of bonds available (three). The node features 821, 822, 823 may each be stated in the form of a matrix.

The relationships between the atoms in the molecule are defined by the adjacency matrix 830. The top row of the adjacency matrix 831 shows all of the atoms in the molecule, and the left column of the matrix 832 shows a list of all possible atoms that can be represented by the matrix for a given set of molecules. In this example, the top row 831 and left column 832 contain the same list of atoms, but in cases where multiple molecules are being represented in the system, the left column may contain other atoms not contained in the particular molecule being represented. The matrix shows, for example, that the hydrogen atom 811 is connected to the carbon atom 812 (a "1" at the intersection of the rows and columns for H and C) and that the carbon atom 812 is connected to the nitrogen atom 813 (a "3" at the intersection of the rows and columns for C and N). In this example, the number of bonds between atoms is represented by the digit in the cell of the matrix. For example, a 1 represents a single bond, whereas a 3 represents a triple bond. In this example, each atom is also self-referenced (a "1" at the intersection of the rows and columns for H and H, C and C, and N and N), but in some embodiments, the self-referencing may be eliminated. In some embodiments, the rows and columns may be transposed (not relevant where the matrix is symmetrical, but relevant where it is not).

Figure 9:
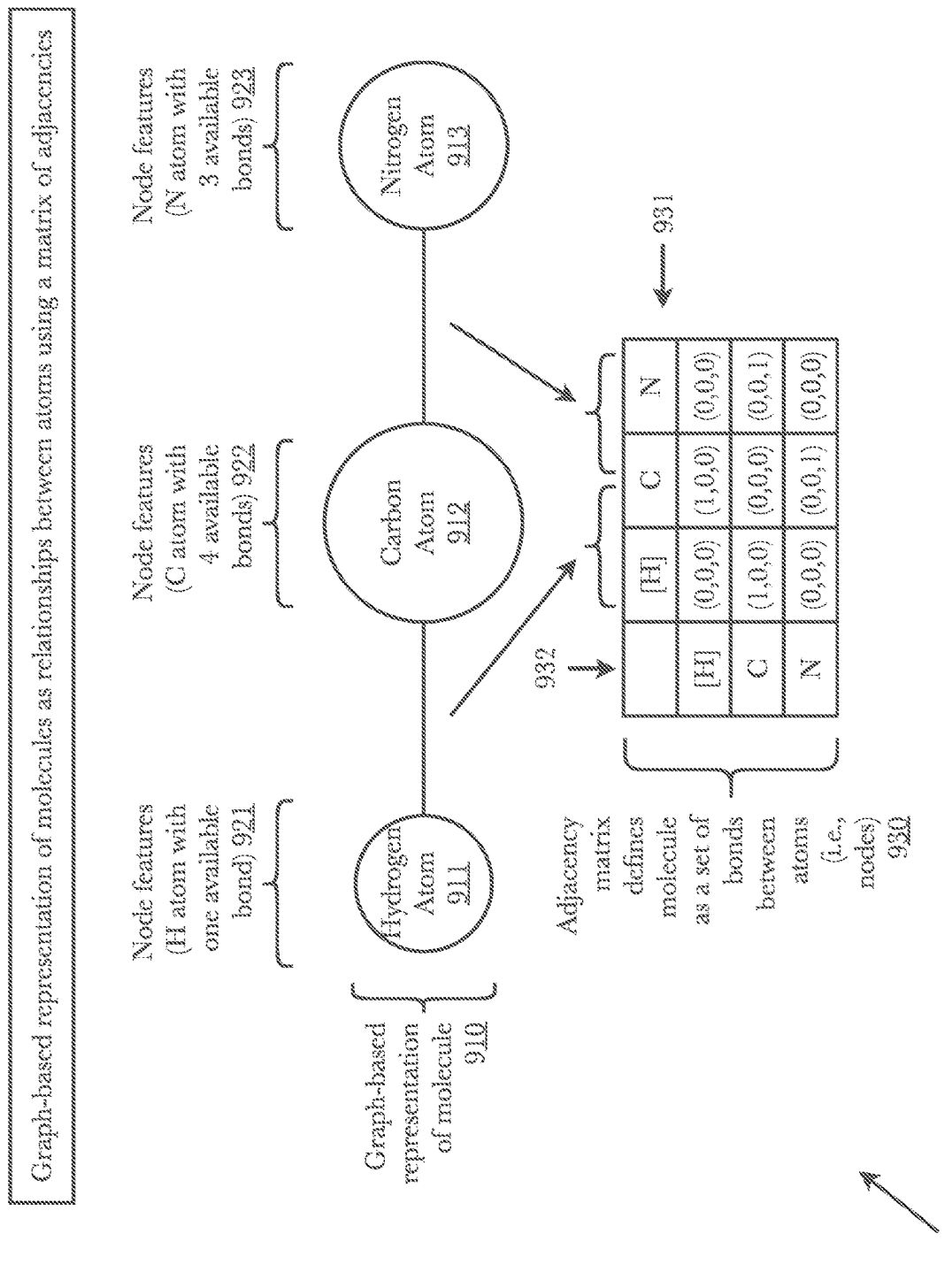
FIG. 9 is a diagram illustrating an exemplary graph-based representation of molecules as relationships between atoms using a matrix of adjacencies using SMILES string encoding and one-hot vectors indicating the types of bonds between atoms.

FIG. 9 is a diagram illustrating an exemplary graph-based representation of molecules as relationships between atoms using a matrix of adjacencies 900, wherein atoms are represented as nodes and bonds between the atoms are represented as edges, and wherein the matrix of adjacencies uses a SMILES string encoding of the molecule and one-hot vector representations of the type of bonds between atoms in the molecule. Representation of molecules as a graph is useful because it provides a of molecular structure which can be processed by graph-based machine learning algorithms like GNNs. Further, the graph-based representation of a molecule can be stated in terms of two matrices, one for the node features (e.g., type of atom and its available bonds) and one for the edges (i.e., the bonds between the atoms). The combination of the nodes (atoms) and edges (bonds) represents the molecule.

In this example, a simple hydrogen cyanide molecule is shown as a graph-based representation 910. A hydrogen cyanide molecule consists of three atoms, a hydrogen atom 911, a carbon atom 912, and a nitrogen atom 913. Its SMILES representation text string is [H]C#N, with the brackets around the H indicating an element other than an organic element, and the # representing a triple bond between the C and N. Each atom in the molecule is shown as a node of a graph. The hydrogen atom 911 is represented as a node with node features 921 comprising the atom type (hydrogen) and the number of bonds available (one). The carbon atom 912 is represented as a node with node features 922 comprising the atom type (carbon) and the number of bonds available (four). The nitrogen atom 913 is represented as a node with node features 923 comprising the atom type (nitrogen) and the number of bonds available (three). The node features 921, 922, 923 may each be stated in the form of a matrix 930.

In this example, the top row 931 and left column 932 contain the same list of atoms, but in cases where multiple molecules are being represented in the system, the left column may contain other atoms not contained in the particular molecule being represented. The matrix 930 shows, for example, that the hydrogen atom 811 is connected to the carbon atom 812 with a single bond (the one-hot vector "(1,0,0)" at the intersection of the rows and columns for H and C) and that the carbon atom 812 is connected to the nitrogen atom 813 with a triple bond (the one-hot vector "(0,0,1)" at the intersection of the rows and columns for C and N). In this example, the number of bonds between atoms is represented by a one-hot vector in the cell of the matrix. For example, a 1 in the first dimension of the vector (1,0,0) represents a single bond, whereas a 1 in the third dimension of the vector (0,0,1) represents a triple bond. In this example, self-referencing of atoms is eliminated, but self-referencing may be implemented in other embodiments, or may be handled by assigning self-referencing at the attention assignment stage. In some embodiments, the rows and columns may be transposed (not relevant where the matrix is symmetrical, but relevant where it is not).

Figure 17:
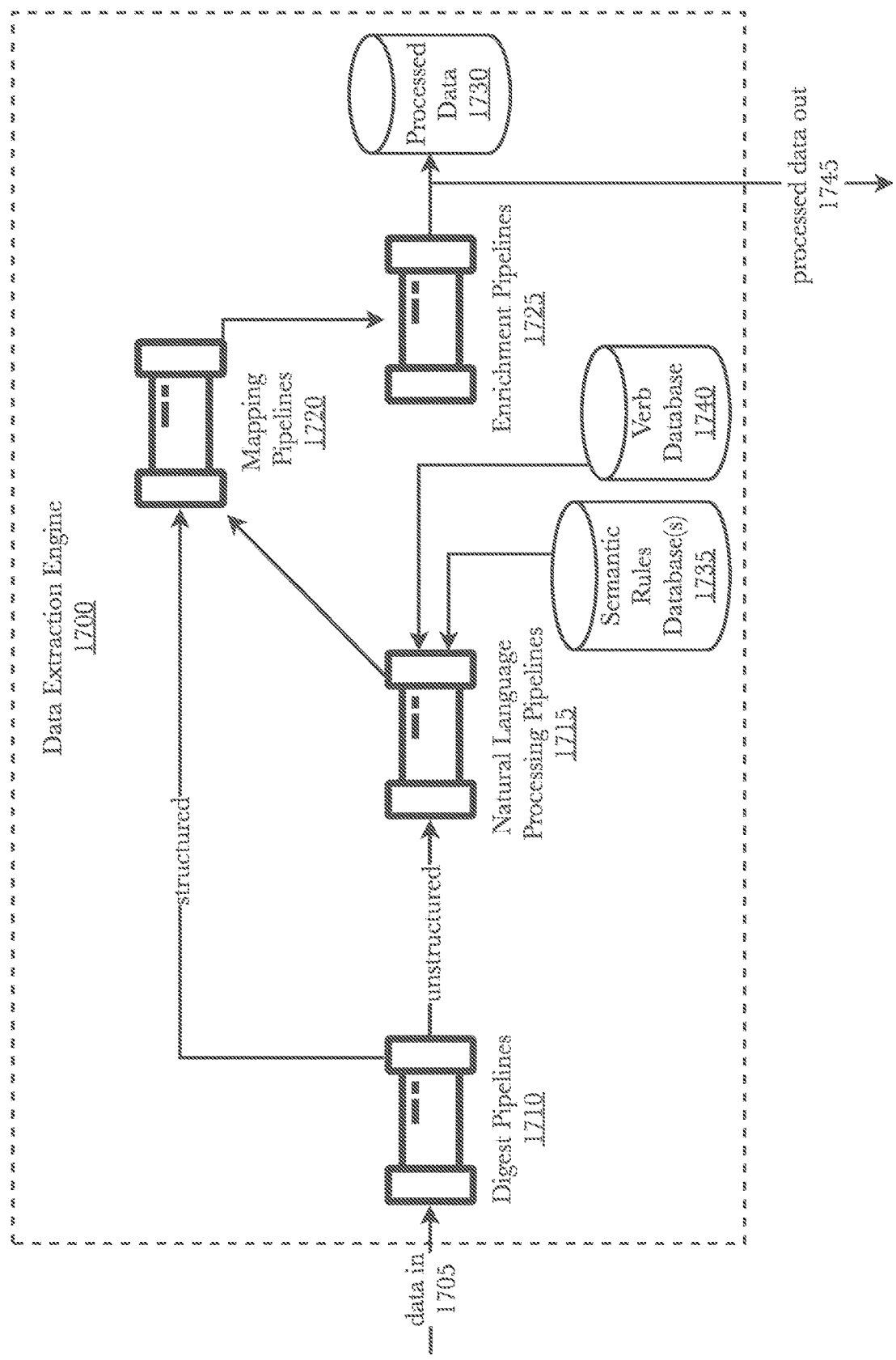
FIG. 17 is a block diagram illustrating an exemplary architecture for an aspect of an automated pharmaceutical research system, the data extraction engine.

FIG. 17 is a block diagram illustrating an exemplary architecture for an aspect of an automated pharmaceutical research system, the data extraction engine 1700. Scraped data passes through data extraction engine 1700 which utilizes a plurality of processing pipelines to extract, process, and enrich the ingested data. According to an embodiment, when information enters data extraction engine 1700 it may be filtered into two categories, structured and unstructured data, and each category has its own processing route. A processing route may be constructed from one or more processing pipelines such as a natural language processing pipeline, a mapping pipeline, and an enrichment pipeline to name a few. The output of a processing route is fully processed data ready to be stored into a database 1730 which stores all data points and for each data point its relational data. Database 1730 may be implemented using any suitable relational database known in the arts. In a preferred embodiment, a postgres system query language (PSQL) object-relational database system is used to store and index all ingested, processed data. A plurality of relational databases may be used to store the ingested data, forming a relational database network. Using a relational database such as PSQL allows for query based searching of the stored and compiled data, which can be used to supplement a variety of functional and analytical tools to retrieve or infer information from a knowledge graph 215 derived from the stored data.

In an embodiment, ingested data enters 1705 the data extraction engine 1700 and enters a digest pipeline 1710. Digest pipeline 1710 parses the received data into two categories, structured and unstructured data. Structured data is highly organized and formatted in a way so it is easily searchable in relational databases. For instance, names, dates, addresses, credit card numbers, quantitative assay results, molecular measurements, gene sequences, clinical trial quantitative data, and protein binding sites are all non-limiting examples of structured data. Unstructured data requires different processing techniques than those used for structured data. Examples of unstructured data include, but is not limited to text such as research paper and medical journal abstracts, video, audio, mobile activity, and satellite imagery. While structured data lends a birds-eye view of a data domain, unstructured data can give a deeper understanding of connections and actors operating within a data domain.

Unstructured data may be sent to natural language processing (NLP) pipelines 1715 where it is parsed and scanned for relevant data to be extracted. Unstructured data may be parsed using common NLP techniques such as non-destructive tokenization, part-of-speech tagging, name entity recognition, sentiment analysis, and syntax-driven sentence segmentation. Unstructured data may be parsed and scanned for a plurality of key words and objects, and verbs that denote relations and directionality between key words and objects (e.g., caused by, leads to, derived from, increases, resists, etc.). The NLP 1715 may conducted using a plurality supervised machine learning algorithms known in the art such as, for example, support vector machines, Bayesian networks, maximum entropy, and conditional random field, or using a plurality of unsupervised machine learning such as clustering, latent semantic indexing, matrix factorization, etc. For example, a research paper regarding the molecular structure of a drug and its efficacy for combating a certain disease may be ingested and sent to NLP pipeline 1715 due to the unstructured format of the document, wherein NLP pipeline 1715 may parse and scan the document title and document abstract for key words such as the drug name and the names of its constituent molecules, disease name, terms related to adverse effects such as nausea, fever, loss of appetite, to name a few, terms related to the severity of the adverse effects (e.g., mild, moderate, etc.) and relational phrases or verbs such as the italicized words in "molecule X configured in Y alignment led to an increase in adverse effect Z". This process may be supported via semantic rules databases 1735 which allows for categorization of the parsed, unstructured data. The semantic rules database 1735 provide exhaustive lists for the types of entities (e.g., gene, protein, drug, disease, etc.) and common synonyms associated with each entity to supplement the NLP 1715 during processing. For example, semantic rules database 1735 may be used to supplement NLP 1715 data extraction with information about the diseases, and allow for tuning of NLP algorithm models based on clustering information on these diseases.

Additionally, the NLP 1715 may access a verbs database 1740 when processing unstructured data in order to identify allowable relationships between entities. Each entity pair has a different set of relationship types (verbs) that define the allowed relationships between each pair (e.g., allowed relationships between drugs and diseases are different from those for drugs and genes). For example, the NLP 1715 may process a given text such as " . . . this study suggests that PIG-S does in fact inhibit development of leukemia in adults . . . " and the model will output "<gene> PIG-S ## inhibit ## <disease> leukemia". In this example, the identified entities are PIG-S, which is assigned a "gene" tag because it was found in a semantic rules database 1735 associated with gene type entities, and leukemia which is assigned the "disease" tag because it was found in the semantic rules database 1735 associate with disease type entities. Likewise, the verb "inhibit" defines the relationship between the identified gene and disease and represents an edge between the identified entity nodes.

The mapping pipelines 1720 receive both structured and NLP processed data and may combine all ingested data sources based on commonality of chemical structure, names, and any relational tables that may be constructed purely based on secondary identification information scraped from the data sources. At this stage of processing all identifiers (IDs) linked to other data sources are retrieved and mapping of all data to as many other data sources as possible is conducted. Each unique data entity (node) is assigned a global identifier which allows the system to collate information from multiple sources, and obtain a fully populated search result page. For example, three databases containing information about proteins are ingested by the automated pharmaceutical research system, and for each ingested database there is a local ID which is used to organize the information. Each of the three databases provide information about the same protein X and the first time protein X is ingested into the system it is given a global ID that is unique to that protein. Each subsequent processing of protein X will be assigned the same global ID, which can be used to collate all available data sources regarding protein X using the global identifier to link a plurality of different data sets to one common data entry (node). Once all data sources have been mapped, then the data from all sources is combined based on the global ID and segregates it into structured tables to breakdown the data. The data then flows from mapping pipelines 1720 into enrichment pipelines 1725 which may perform data interpolation actions by combining all ingested data sources and comparing common values, or filling the empty values with the full value from another ingested data source. As data exits enrichment pipelines 1725 it is stored as processed data in a relational database 1730 of the proper entity domain as determined by the assigned global ID, and sent out 1745 to knowledge graph constructor 213 and vector extraction and embedding 216.

Figure 18:
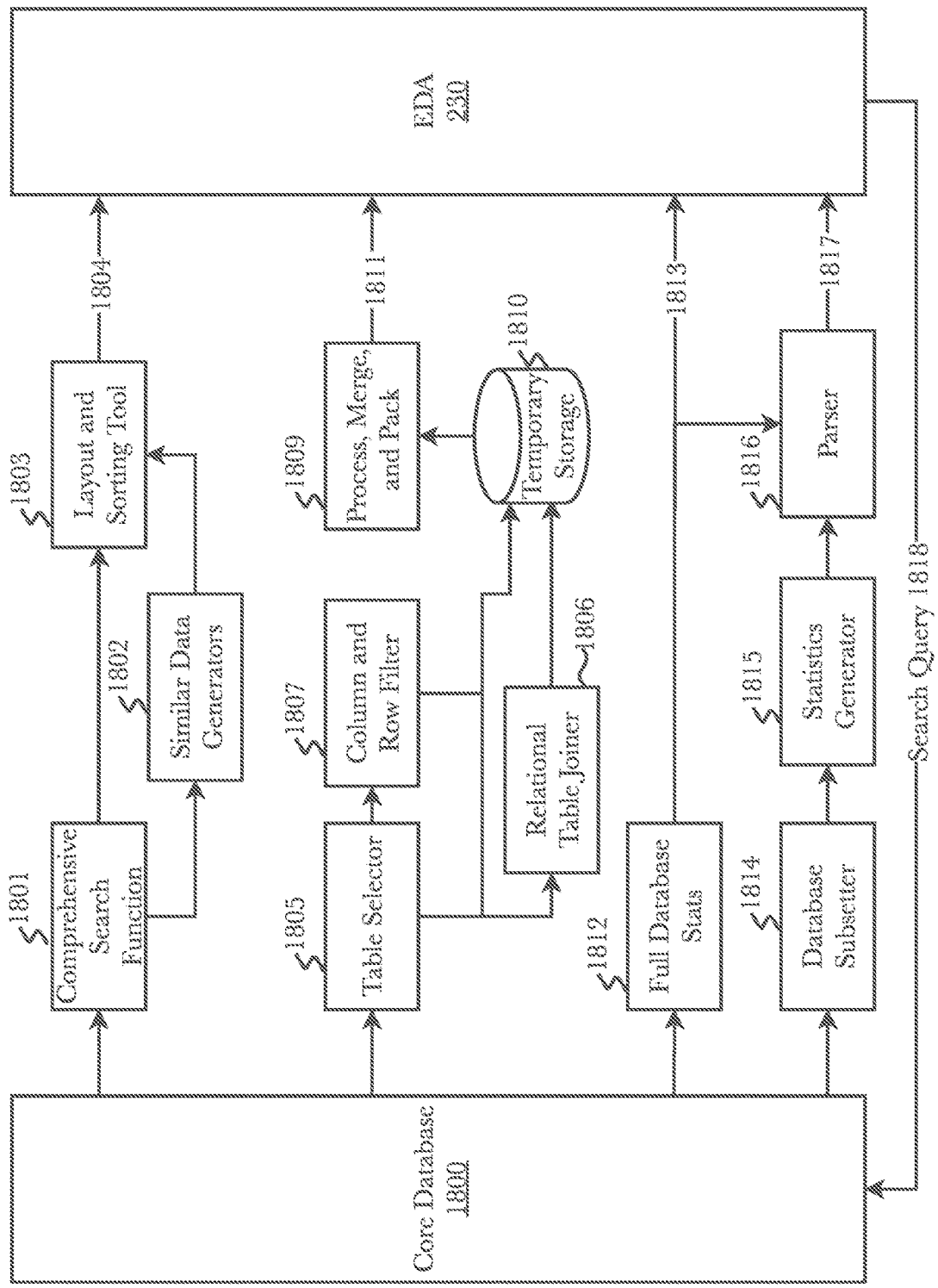
FIG. 18 is a block diagram illustrating an exemplary system architecture for an embodiment of a pharmaceutical research system showing the workflow for populating a search result page associated with a search query.

FIG. 18 is a block diagram illustrating an exemplary system architecture for an embodiment of a pharmaceutical research system showing the workflow for populating a search result page associated with a search query. A system user may access the EDA 230 and submit a search query 1818 to the core database 1800 of the pharmaceutical research data platform. The core database 1800 may contain scraped, ingested, and extracted data from both public and private data sources which is used to create a massive relational network wherein a custom built knowledge graph is derived from the information contained in the core database 1800. When a search query 1818 is submitted a comprehensive search function 1801 locates, retrieves the most relevant data related to the parameters of the search query, and returns in priority order the relevant data. For example, a search query for a specific accession (i.e. number in bioinformatics that is a unique identifier given to a DNA or protein sequence) will return data on the specific protein related to the queried accession number, as opposed to the first return result being an assay that contains that accession number. The returned data may be sent to similar data generators 1802 where a plurality of similarity search functions may be used to identify similarly related data to the search query. For example, comparing binary fingerprints using a Tanimoto search may identify similar molecules related to the search query, likewise, comparing FASTA string representations of proteins may identify similar proteins related to the search query. Additionally, the system may dynamically create vectors and embeddings representing the data entries (nodes) of knowledge graph and then use vector based machine learning algorithms to determine the similarity (i.e. distance) between vectors from the same data category. The retrieved data, and any similarity search data is sent to a layout and sorting tool 1803 which prepares the retrieved data for presentation in the EDA 230 frontend. The search engine results 1804 are sorted into groups with links to data that cannot be displayed and a section of similar data.

The returned search engine results also provide the retrieved data in comma separated variable (CSV) format. A table selector 1805 may be used to retrieve relational tables specific to the search query 1818 stored within the core database 1800. The retrieved relational tables may pass through a series of column and row filters 1807 that may be used to provide only information relevant the search query 1818. Multiple tables are sent to the relational table joiner 1806 which combines the columns of the retrieved relational tables to form a new table of information specific to the search query. The new table and the filtered data is stored in temporary storage 1810 where it may be quickly accessed during the processing, merging and packing 1809 step which outputs 1811 a user tailored merged CSV file, or a bundle of CSVs.

Additionally, a search result page may also contain graphs and statistics relevant to the search query. Full database statistics 1812 may be retrieved and displayed 1813 to allow a user to interact with and navigate through the entire core database 1800. To display graphs and statistics specific to the search query a database subsetter 1814 that copies only a portion of data related to the search query from the core database, while maintaining the relational data associated with the selected portion of data. The subsets of data may be sent to a statistics generator 1815 which may perform, for any subset or search, a variety of statistical calculations and create graphs to visually represent the results of the search query. The generated statistics and graphs, as well as the full database statistics, are passed to a parser 1816 which may identify overlapping statistical and graphical representations. For any subset or search, the output 1817 is a set of graphics and statistics for that particular action which may then be displayed on the search result page returned in response to a search query. While this simplified diagram does not purport to show all types of search queries that may be generated or all search processes that may be relevant, it does show certain important data retrieval and processing steps for populating a search result page for a pharmaceutical research system.

Figure 20:
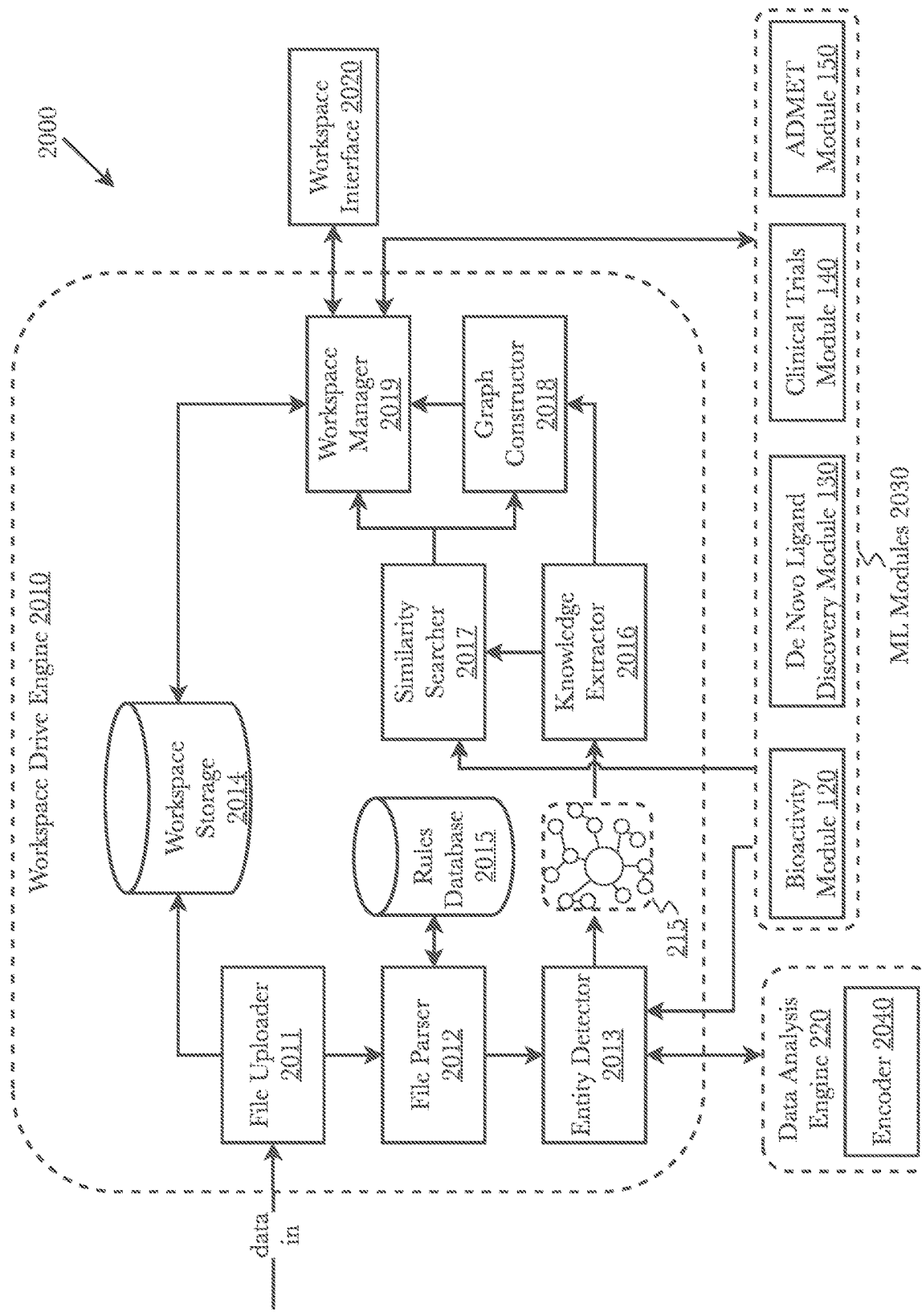
FIG. 20 is a block diagram illustrating an exemplary system architecture for an automated pharmaceutical research with context workspaces system, according to a preferred embodiment.

FIG. 20 is a block diagram illustrating an exemplary system architecture for an automated pharmaceutical research with context workspaces system 2000, according to a preferred embodiment. According to an embodiment, context workspace system 2000 may comprise a workspace drive engine 2010 which may analyze uploaded data files to automatically detect biochemical and biomedical entities contained within the uploaded data file and extract information related to the biochemical and biomedical entities and then format the extracted information for display on a research workspace, a data analysis engine 220 which may create abstract vector representations of novel biochemical and biomedical entities and identify at least one similar prior existing biochemical or biomedical entity, a plurality of ML modules 2030, and workspace interface 2020 which provides a system user with a means to interact with the workspace drive system and its components and processes.

According to an embodiment, a system user (i.e., researcher) utilizes a workspace interface 2020 to create a research workspace or to access an existing workspace. One use of a research workspace is to provide a pharmaceutical or biomedical researcher with a plurality of historical and inferred information in order to better contextualize his or her current research. For example, workspace interface 2020 may provide a means for a researcher to upload data files containing data related to one or more biochemical and biomedical entities (e.g., genes, proteins, molecules, drugs, etc.). Then workspace drive engine 2010 can automatically extract all information related to the uploaded data and return the extracted information to the researcher's workspace. At that point, a researcher may be able to explore the extracted information through similarity searches, a plurality of machine learning modules 2030, and graph-based tools for exploring knowledge graph 215 and other graphs that may be generated specifically for a given workspace. All extracted data, researcher uploaded data, similarity search results, ML modules 2030 output, and query results may be saved to a workspace and stored in workspace storage 2014. In this way, workspace drive system 2000 provides a researcher with a secure virtual workspace that leverages the pharmaceutical research system (referring to FIG. 1) to provide a large plurality of information that allows a researcher to frame their research in the context of current pharmaceutical research.

According to an embodiment, a system user (i.e., researcher) may upload his or her own data files to the automated pharmaceutical research system via a file uploader 2011. Uploaded data files may comprise various file and data formats including, but not limited to, text files (e.g., Word documents, ASCII files, rich text files, etc.), JavaScript Object Notation (JSON) files, extensible markup language (XML) files, spreadsheet files, and portable document format (PDF) files, to name a few. Once a data file has been uploaded, a copy of the data file may be stored in workspace storage 2014 for future use. Workspace storage 2014 may be used to store and retrieve system user workspaces. According to an embodiment, user workspaces may include user uploaded data files, data automatically extracted from the knowledge graph 215 related to the uploaded data files, and any machine learning outputs that may have been generated in response to the uploaded data files.

According to an embodiment, a file parser 2012 may be implemented which can receive and read an uploaded data file to extract the data contained therein. For example, a CSV (Comma-Separated Value) parser reads a stream structured according to the rules of CSV (e.g., commas, quoting, etc.) to extract the data items represented by each line in the file. File parser 2012 may comprise a plurality of different parsers configured to parse different file formats. In some embodiments, file parser 2012 may comprise a single, reconfigurable parser optimized for accuracy and recurrent reconfigurability, and may be able to retrieve applicable file format rules from a rules database 2015 in order to execute a file parser reconfiguration. File parser 2012 may send parsed data to an entity detector 2013.

According to an embodiment, an entity detector 2013 automatically detects biochemical and biomedical entities (e.g., FASTA sequences, various database IDs, protein or gene name, etc.) within the uploaded data file by conducting an entity match analyzing the parsed data to match it with any possible existing biochemical and biomedical entities contained within knowledge graph 215. An entity match may be performed by doing a keyword search against the all the data contained within the pharmaceutical research platform, wherein a parsed biochemical or biomedical entity from the uploaded data file may be used as the keyword. An entity match may be conducted against information stored in the biochemical database(s) 214, and/or against the knowledge graph 215. In other embodiments, an entity match may be conducted by adding the parsed biochemical or biomedical entity to the knowledge graph 215 and then conducting a cluster analysis on the graph to identify existing biochemical and biomedical entities that map to the parsed biochemical or biomedical entity within the same cluster space. For example, an uploaded data file that contains a comma-separated list of biochemical entities is parsed by file parser 2012 and each parsed data is sent to entity detector 2013 which detects the received data is a FASTA sequence, or RORG_HUMAN, or P51449, which all map to the same biochemical entity, which is a protein called "Nuclear receptor ROR-gamma", and has a data platform global ID of 16201651449.

According to an embodiment, parsed biochemical and biomedical entities that are undetected (i.e., no match was found between a parsed biochemical entity and existing biochemical entities) as already existing within the knowledge graph 215 or biochemical database(s) 214 may be sent by entity detector 2013 to a data analysis engine 220. Data analysis engine 220 may comprise an encoder 2040 trained on a subset of the data stored in a relational database (e.g., biochemical database(s) 214) to identify the key features that define the data stored in the relational database. The trained encoder 2040 can be used to create an abstract latent space represented as a three-dimensional convolutional neural network, wherein the abstract latent space contains vectorized representations of all data points in the relational database. Data analysis engine 220 may receive an undetected biochemical or biomedical entity from entity detector 2013 and input the undetected biochemical or biomedical entity into the trained encoder 2040 to create an abstract vector representation of the undetected biochemical or biomedical entity, which exists in the abstract latent space of the three-dimensional convolutional neural network. Data analysis engine 220 may then compute the distance between the vector representation of the undetected biochemical or biomedical entity and other abstract vectors with the latent space and then compare the computed distance to a predetermined threshold of similarity. If the computed distance is greater than the threshold it indicates similarity between the vectors. Data analysis engine 220 may then decode the abstract vector that is greater that the threshold and return the data related to the decoded vector. Returned data may be sent to workspace manager 2019 for display in the workspace where the data file was uploaded. In this way, a researcher may be able to upload her research data in order to gather all available data related to the uploaded research data, the gathered data may be used by the researcher to better understand her research in the context of existing and inferred pharmaceutical and bio-informational research.

A knowledge extractor 2016 may extract all of the relevant information about the detected biochemical and biomedical entities and concepts, as it relates to the knowledge graph 215. Knowledge extractor 2016 may also extract the vector representation of the detected biochemical entities and associated concepts. Extracted information and vector representations may be sent to a graph constructor 2018 so that one or more graph representations of the extracted data may be generated.

According to an embodiment, knowledge extractor 2016 may send extracted vector representations of detected biochemical and biomedical entities and associated concepts to a similarity searcher 2017. Similarity searcher 2017 may execute at least one of the various built-in similarity searches implemented by the automated pharmaceutical research system (referring to FIG. 1). For example, Tanimoto or substructure similarity searches for molecules, BLAST searches for similar proteins, binding site similarity, latent space vectorization similarity, etc. The results of executed similarity searches may be sent to graph constructor 2018, and to a workspace manager 2019.

Graph constructor 2018 may receive extracted information and vector representations of that information, similarity search result information, and information about the one or more biochemical and biomedical entities contained within the uploaded data file. Graph constructor 2018 may be configured to create a plurality of types of graphs such as, for example, knowledge graphs, time-series graphs, relational graphs, statistical graphs, and the like. For example, a researcher creates a workspace and uploads a data file containing characteristic information about a novel molecule, graph constructor 2018 can create a knowledge graph based on the uploaded novel molecule and how it relates to existing biochemical and biomedical entities (e.g., molecules, genes, proteins, assays, clinical trials, etc.), and then send the created knowledge graph to workspace manager 2019 where the researcher could view and interact with the knowledge graph via a workspace interface 2020. Additionally, according to some embodiments, workspace manager 2019 may also provide graph-based visualization tools to show the similar biochemical and biomedical entities through experimental and inferred relationships. For example, a researcher may be able to view a knowledge graph derived from her workspace data based only on experimental relationships determined from the large plurality of literature data ingested and processed by data curation platform 210, and/or she could view a knowledge graph derived from her workspace data and inferred relationships determined from machine and deep learned models and simulations.

According to an embodiment, workspace manager 2019 may receive, retrieve, or otherwise obtain a plurality of data from various sources and serve as an intermediary between workspace drive engine 2010 components and a frontend user workspace interface 2020. Workspace manager 2019 may also format received data for display, as well as configure workspace layout during workspace creation. Workspace interface 2020 may be a graphic user interface (GUI) accessible via a computing device such as a computer, laptop, tablet, and smart phone. Workspace interface 2020 may be accessible via a mobile device software application (app) and/or via a webapp on the internet, and provide a system 2000 user to access his or her workspace storage 2014 data, create a new workspace, open an existing workspace, save a workspace, upload data files, search the pharmaceutical and biomedical research platform for information, conduct similarity searches, and run machine and deep learning algorithms on uploaded data. Selecting or conducting any of these actions via workspace interface 2020 may generate a request to workspace manager 2019. Workspace manager 2019 may then query and retrieve the relevant data or execute the correct process responsive to the generated request. For example, a researcher may select a "RUN ML" button on the workspace interface 2020 which sends a request to workspace manager 2019 to execute one or more of the machine learning modules 2030 using the data specified by the researcher, the output of the ML modules 2030 may be sent to workspace manager 2019 where it may be formatted for display on the workspace interface 2020. Furthermore, processes, actions and outputs from ML modules 2030 may be feedback into knowledge graph 215 via entity detector 2013 and/or similarity searcher 2017. In this way, as new knowledge is discovered or generated via ML modules 2030 can be captured and applied to knowledge graph 215.

Workspace drive engine 2010 may be integrated with one or more ML modules 2030 which can provide workspace users with predictions and optimizations targeted at entities of their choice. For instance, a researcher may want to obtain Bioactivity 120 predictions after identifying a protein of interest that was identified using the automated pharmaceutical research system, or that was inputted by uploading a data file. A researcher could immediately click "RUN ML ASSAYS" on an entry page to get these predictions and immediately send them to the researcher's workspace and store them in the researcher's workspace storage 2014. For example, these predictions may include: bioactivity 120 with a given protein sequence (FASTA-based) or a binding site (3-Dimensional), ligand-based De Novo 130 with a set of active ligands identified on the automated pharmaceutical research system or uploaded, and pocket-based De Novo 130 with an identified or uploaded binding site of a target disease.

DETAILED DESCRIPTION OF EXEMPLARY ASPECTS

Figure 10:
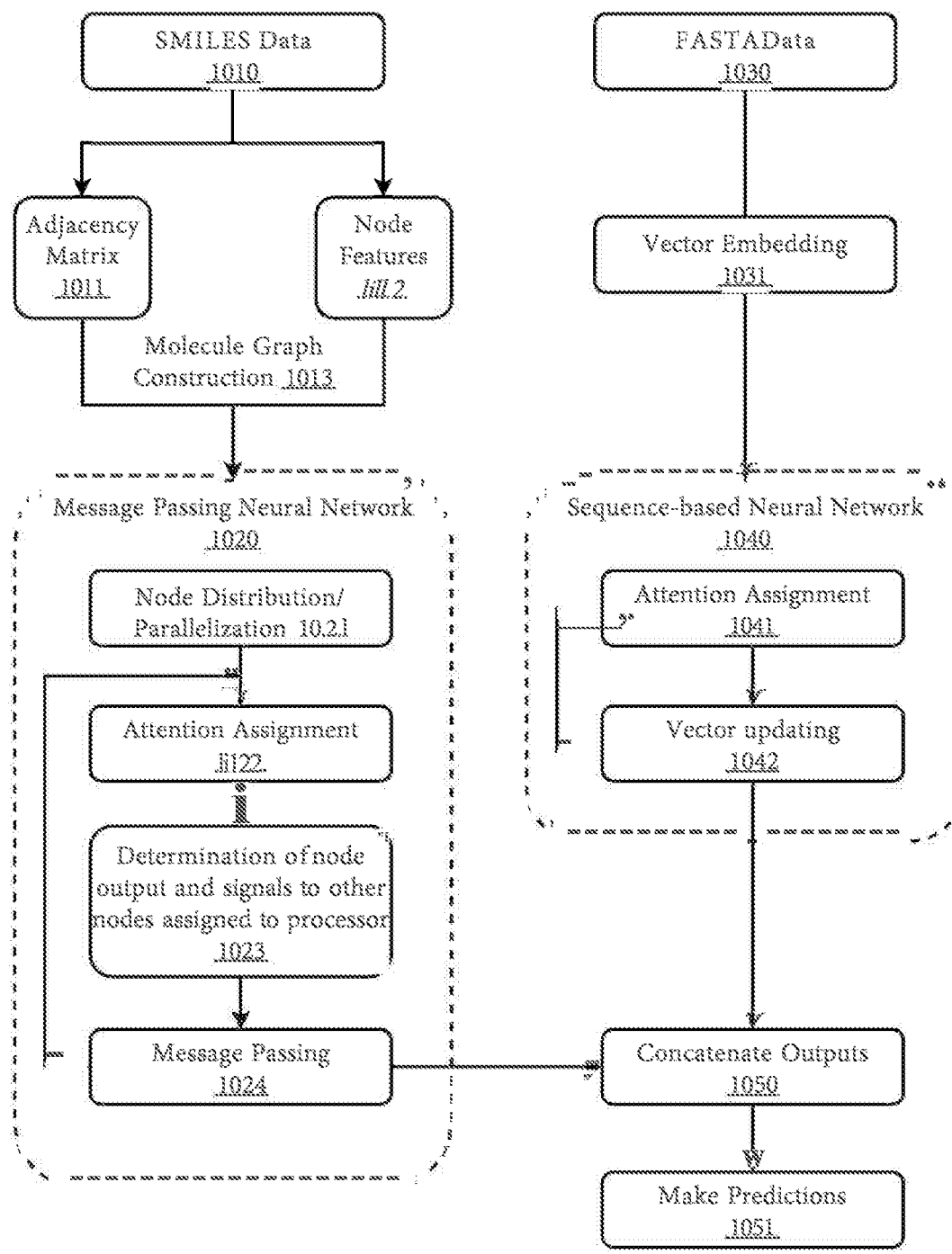
FIG. 10 is a diagram illustrating an exemplary architecture for prediction of molecule bioactivity using concatenation of outputs from a graph-based neural network which analyzes molecule structure and a sequence-based neural network which analyzes protein structure.

FIG. 10 is a diagram illustrating an exemplary architecture for prediction of molecule bioactivity using concatenation of outputs from a graph-based neural network which analyzes molecules and their known or suspected bioactivities with proteins and a sequence-based neural network which analyzes protein segments and their known or suspected bioactivities with molecules. In this architecture, in a first neural network processing stream, SMILES data 1010 for a plurality of molecules is transformed at a molecule graph construction stage 1013 into a graph-based representation wherein each molecule is represented as a graph comprising nodes and edges, wherein each node represents an atom and each edge represents a connection between atoms of the molecule. Each node represents the atom as node features comprising an atom type and a number of bonds available for that atom. The node features are represented as a node features matrix 1012. The molecule, then, is represented as nodes (atoms) connected by edges (bonds), and is specified as an adjacency matrix 1011 showing which nodes (atoms) are connected to which other nodes (atoms).

At the training stage, the adjacency matrices 1011 and node features matrices 1012 for many molecules are input into the MPNN 1020 along with vector representations of known or suspected bioactivity interactions of each molecule with certain proteins. Based on the training data, the MPNN 1020 learns the characteristics of molecules and proteins that allow interactions and what the bioactivity associated with those interactions is. At the analysis stage, a target molecule is input into the MPNN 1020, and the output of the MPNN 1020 is a vector representation of that molecule's likely interactions with proteins and the likely bioactivity of those interactions.

Once the molecule graph construction 1013 is completed, the node features matrices 1012 and adjacency matrices 1011 are passed to a message passing neural network (MPNN) 1020, wherein the processing is parallelized by distributing groups 1021 nodes of the graph amongst a plurality of processors (or threads) for processing. Each processor (or thread) performs attention assignment 1022 on each node, increasing or decreasing the strength of its relationships with other nodes, and outputs of the node and signals to other neighboring nodes 1023 (i.e., nodes connected by edges) based on those attention assignments are determined. Messages are passed 1024 between neighboring nodes based on the outputs and signals, and each node is updated with the information passed to it. Messages can be passed between processors and/or threads as necessary to update all nodes. In some embodiments, this message passing (also called aggregation) process is accomplished by performing matrix multiplication of the array of node states by the adjacency matrix to sum the value of all neighbors or divide each column in the matrix by the sum of that column to get the mean of neighboring node states. This process may be repeated an arbitrary number of times. Once processing by the MPNN is complete, its results are sent for concatenation 1050 with the results from a second neural network, in this case a long short term memory neural network 1040 which analyzes protein structure.

In a second processing stream, FASTA data 1030 is converted to high-dimensional vectors 1031 representing the amino acid structure of proteins. The vectors are processed by a long short term memory (LS™) neural network 1040 which performs one or more iterations of attention assignment 1041 and vector updating 1042. The attention assignment 1041 of the LS™ 1040 operates in the same way as that of the MPNN 1020, although the coding implementation will be different. At the vector updating stage 1042, the vectors comprising each cell of the LSTM 1040 are updated based on the attention assignment 1041. This process may be repeated an arbitrary number of times. Once processing by the LSTM 1040 is complete, its results are sent for concatenation 1050 with the results from the first processing stream, in this case the MPNN 1020.

Concatenation of the outputs 1050 from two different types of neural networks (here an MPNN 1020 and an LSTM 1040) determines which molecule structures and protein structures are compatible, allowing for prediction of bioactivity 1051 based on known or suspected similarities with other molecules and proteins.

Figure 11A:
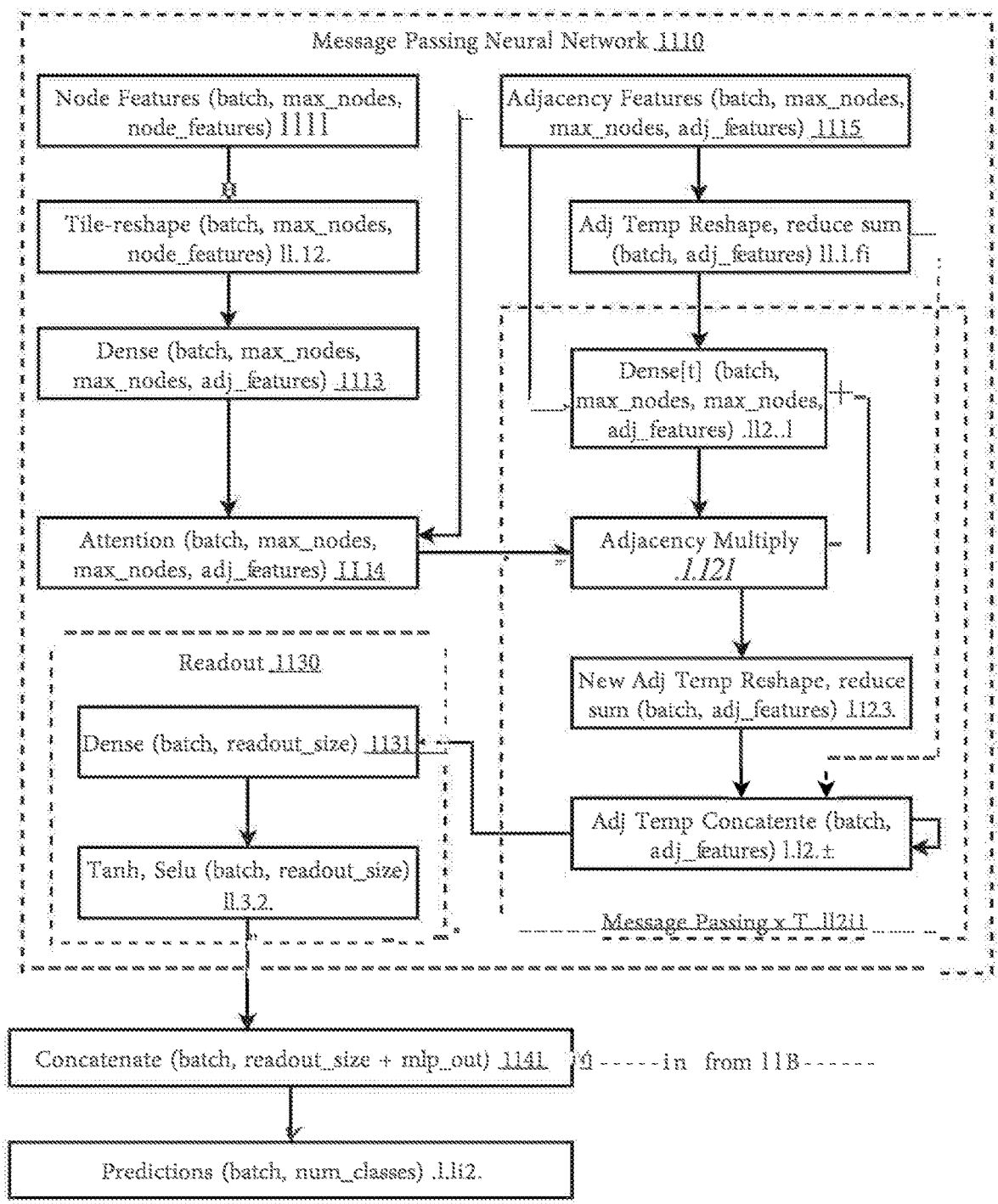
FIGS. 11A and 11B illustrates an exemplary implementation of an architecture for prediction of molecule bioactivity using concatenation of outputs from a graph-based neural network which analyzes molecule structure and a sequence-based neural network which analyzes protein structure.
Figure 11B:
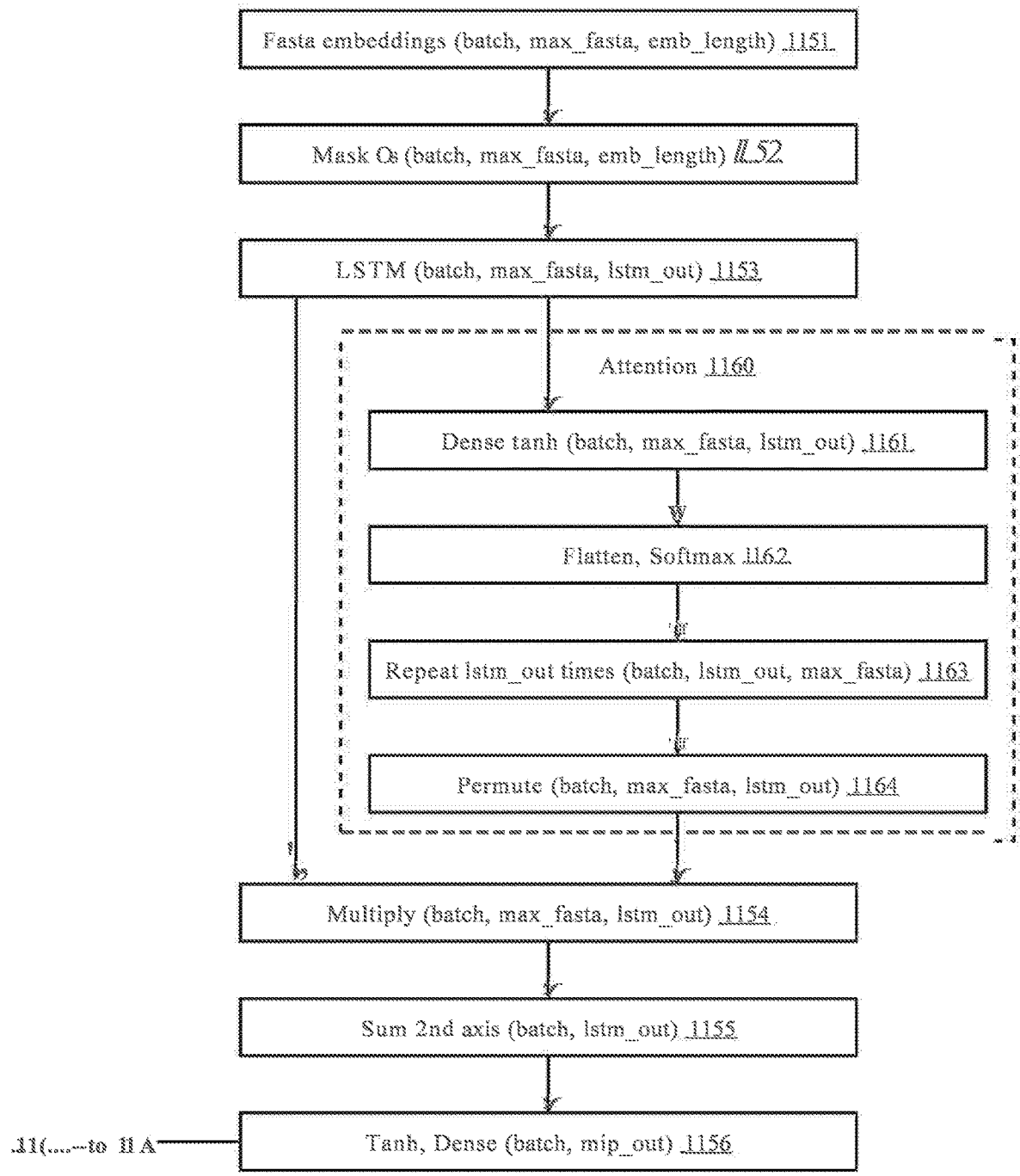

FIGS. 11A and 11B illustrate an exemplary implementation of the architecture for prediction of molecule bioactivity using concatenation of outputs from a graph-based neural network which analyzes molecule structure and a sequence-based neural network which analyzes protein structure. In this example, details regarding a particular implementation of the general architecture shown in FIG. 10 are described.

As shown in FIG. 11A, node features 1111 are received for processing. A reshaping process 1112 may be performed which to conform the dimensionality of the inputs to the dimensionality required for processing by the MPNN. A dense function 1113 is performed to map each node in the previous layer of the neural network to every node in the next layer. Attention is then assigned 1114 using the adjacency matrix contained in the node. The adjacency features (the adjacency matrix) 1115 are simultaneously reshaped 1116 to conform the dimensionality of the inputs to the dimensionality required for processing by the MPNN.

At this stage, a message passing operation 1120 is performed, comprising the steps of performing a dense function 1121 (used only on the first message pass) to map each node in the previous layer of the neural network to every node in the next layer, matrix multiplication of the adjacencies 1122, reshaping of the new adjacencies 1123, and where the message passing operation has been parallelized among multiple processors or threads, concatenating the outputs of the various processors or threads 1124.

Subsequently, a readout operation 1130 is performed comprising performance of a dense function 1131 and implementation of an activation function 1132 such as tanh, selu, etc. to normalize the outputs to a certain range. In this embodiment, the readout operation 1130 is performed only at the first message pass of the MPNN 1110.

As shown in FIG. 11B, FASTA data is converted to high-dimensional vectors 1151, which may then be masked 1152 to conform the vectors to the fixed input length required by the LSTM 1153. The LSTM 1153 then processes the vectors using an attention mechanism 1160 comprising the steps of performing a dense function 1161 to map each node in the previous layer of the neural network to every node in the next layer, performing a softmax function 1162 to assign probabilities to each node just before the output layer. The process is repeated a number of times which may be configured by a parameter 1163. Where permutation invariance is an issue (i.e., where changes in the order of inputs yield changes in the outputs), permutations may be applied to the inputs 1164 to ensure that differences in outputs due to differences in inputs are incorporated.

After attention has been assigned 1160, the vectors in the cells of the LSTM 1153 are multiplied 1154, summed 1155, and a dense function 1156 is again applied to map each node in the previous layer of the neural network to every node in the next layer, and the outputs of the LSTM 1153 are sent for concatenation 1141 with the outputs of the MPNN 1110, after which predictions can be made 1142.

Figure 12:
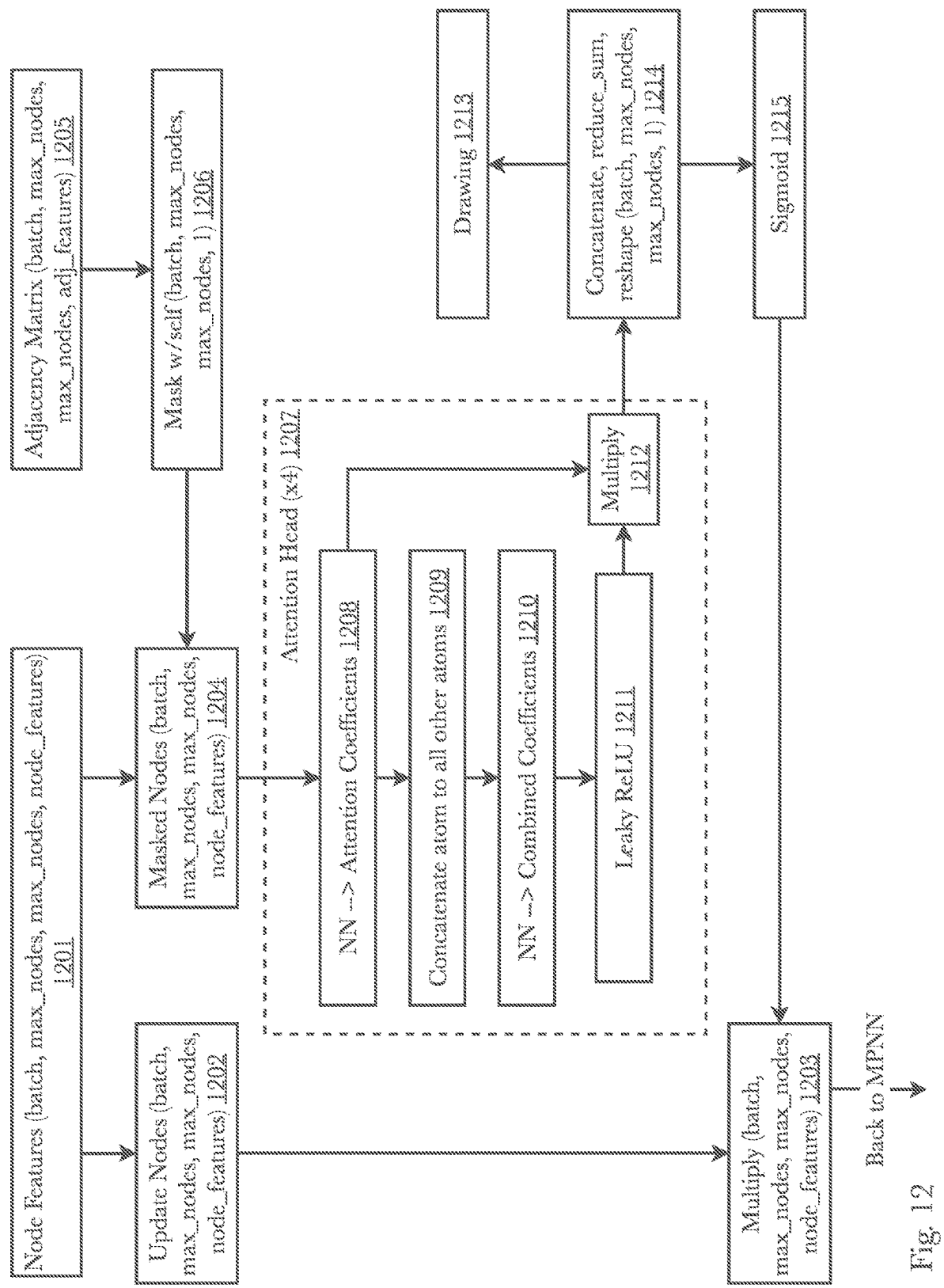
FIG. 12 illustrates an exemplary implementation of the molecule attention assignment aspect of an architecture for prediction of molecule bioactivity using concatenation of outputs from a graph-based neural network which analyzes molecule structure and a sequence-based neural network which analyzes protein structure.

FIG. 12 illustrates an exemplary implementation of an attention assignment aspect of an architecture for prediction of molecule bioactivity using concatenation of outputs from a graph-based neural network which analyzes molecule structure and a sequence-based neural network which analyzes protein structure. In this example, details regarding a particular implementation of the attention assignment blocks shown in FIG. 10 are described. The particular implementation of this example involves a multi-head attention mechanism.

As node features 1201 are received for processing, they are updated 1202 and sent for later multiplication 1203 with the outputs of the multiple attention heads 1207. Simultaneously, the nodes are masked 1204 to conform their lengths to a fixed input length required by the attention heads 1207. The adjacency matrix 1205 associated with (or contained in) in each node is also masked 1206 to conform it to a fixed length and sent along with the node features to the multi-head attention mechanism 1207.

The multi-head attention mechanism 1207 comprises the steps of assigning attention coefficients 1208, concatenating all atoms to all other atoms 1209 (as represented in the adjacency matrix), combining the coefficients 1210, performing a Leaky ReLU 1211 function to assign probabilities to each node just before the output layer, and performing matrix multiplication 1212 on the resulting matrices.

The outputs of the multi-head attention mechanism 1207 are then concatenated 1214, and optionally sent to a drawing program for display of the outputs in graphical form 1213. A sigmoid function 1215 is performed on the concatenated outputs 1214 to normalize the outputs to a certain range. The updated node features 1202 are then multiplied 1203 with the outputs of the multi-head attention mechanism 1207, and sent back to the MPNN.

Figure 13:
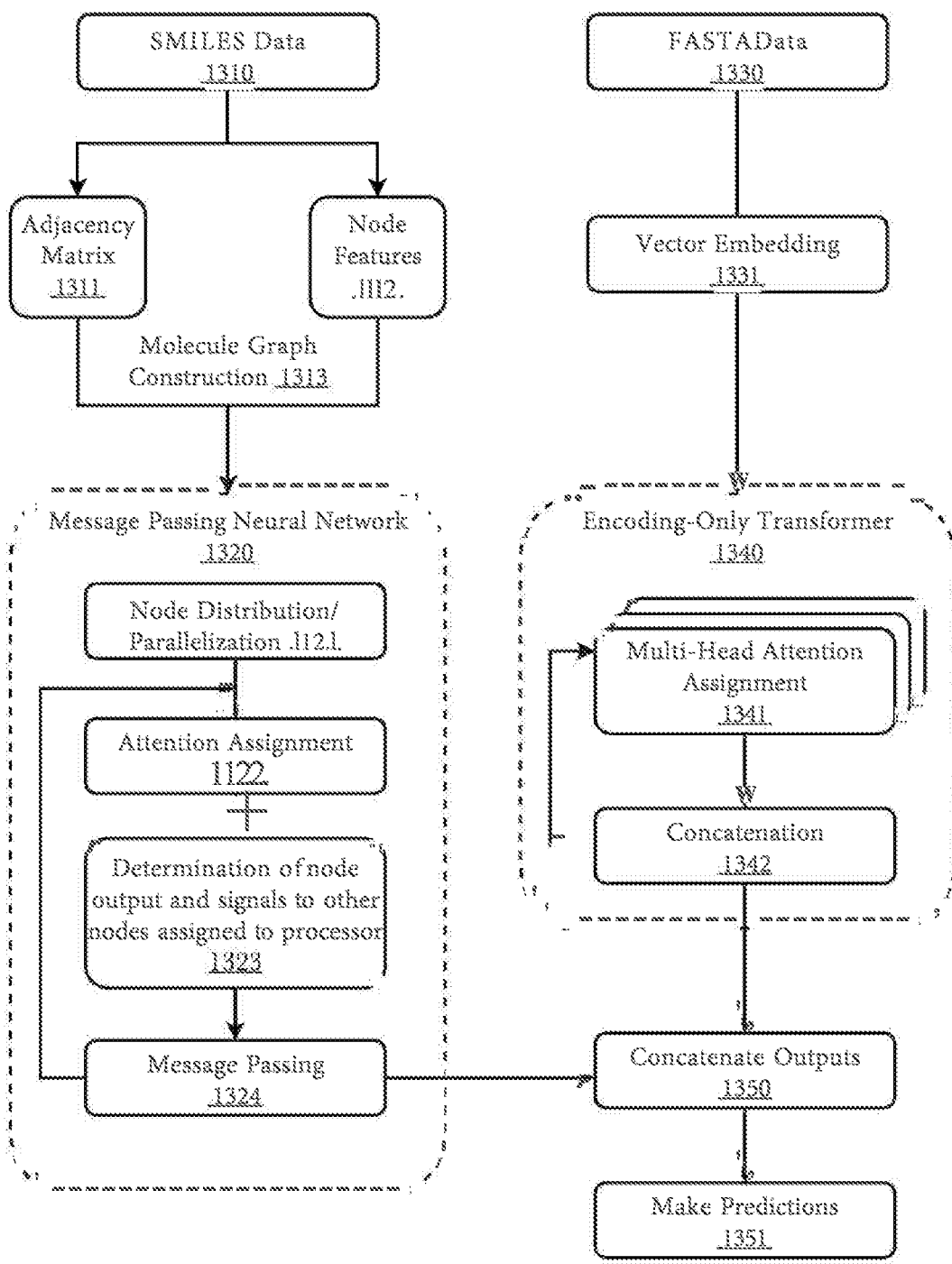
FIG. 13 is a diagram illustrating an exemplary architecture for prediction of molecule bioactivity using concatenation of outputs from a graph-based neural network and an attention-based transformer.

FIG. 13 is a diagram illustrating an exemplary architecture for prediction of molecule bioactivity using concatenation of outputs from a graph-based neural network which analyzes molecules and their known or suspected bioactivities with proteins and a sequence-based neural network which analyzes protein segments and their known or suspected bioactivities with molecules. In this architecture, in a first neural network processing stream, SMILES data 1310 for a plurality of molecules is transformed at a molecule graph construction stage 1313 into a graph-based representation wherein each molecule is represented as a graph comprising nodes and edges, wherein each node represents an atom and each edge represents a connection between atoms of the molecule. Each node represents the atom as node features comprising an atom type and a number of bonds available for that atom. The node features are represented as a node features matrix 1312. The molecule, then, is represented as nodes (atoms) connected by edges (bonds), and is specified as an adjacency matrix 1311 showing which nodes (atoms) are connected to which other nodes (atoms).

At the training stage, the adjacency matrices 1311 and node features matrices 1312 for many molecules are input into the MPNN 1320 along with vector representations of known or suspected bioactivity interactions of each molecule with certain proteins. Based on the training data, the MPNN 1320 learns the characteristics of molecules and proteins that allow interactions and what the bioactivity associated with those interactions is. At the analysis stage, a target molecule is input into the MPNN 1320, and the output of the MPNN 1320 is a vector representation of that molecule's likely interactions with proteins and the likely bioactivity of those interactions.

Once the molecule graph construction 1013 is completed, the node features matrices 1012 and adjacency matrices 1011 are passed to a message passing neural network (MPNN) 1020, wherein the processing is parallelized by distributing groups 1321 nodes of the graph amongst a plurality of processors (or threads) for processing. Each processor (or thread) performs attention assignment 1322 on each node, increasing or decreasing the strength of its relationships with other nodes, and outputs of the node and signals to other neighboring nodes 1323 (i.e., nodes connected by edges) based on those attention assignments are determined. Messages are passed between neighboring nodes based on the outputs and signals, and each node is updated with the information passed to it. Messages can be passed 1324 between processors and/or threads as necessary to update all nodes. In some embodiments, this message passing (also called aggregation) process is accomplished by performing matrix multiplication of the array of node states by the adjacency matrix to sum the value of all neighbors or divide each column in the matrix by the sum of that column to get the mean of neighboring node states. This process may be repeated an arbitrary number of times. Once processing by the MPNN is complete, its results are sent for concatenation 1350 with the results from a second machine learning algorithm, in this case an encoding-only transformer 1340.

In a second processing stream, FASTA data 1330 is converted to high-dimensional vectors 1331 representing the chemical structure of molecules. The vectors are processed by an encoding-only transformer 1340 which performs one or more iterations of multi-head attention assignment 1341 and concatenation 1342. Once processing by the encoding-only transformer 1340 is complete, its results are sent for concatenation 1350 with the results from the neural network, in this case the MPNN 1320.

Concatenation of the outputs 1350 from two different types of neural networks (here an MPNN 1320 and an LSTM 1340) determines which molecule structures and protein structures are compatible, allowing for prediction of bioactivity 1351 based the information learned by the neural networks from the training data.

Figure 14:
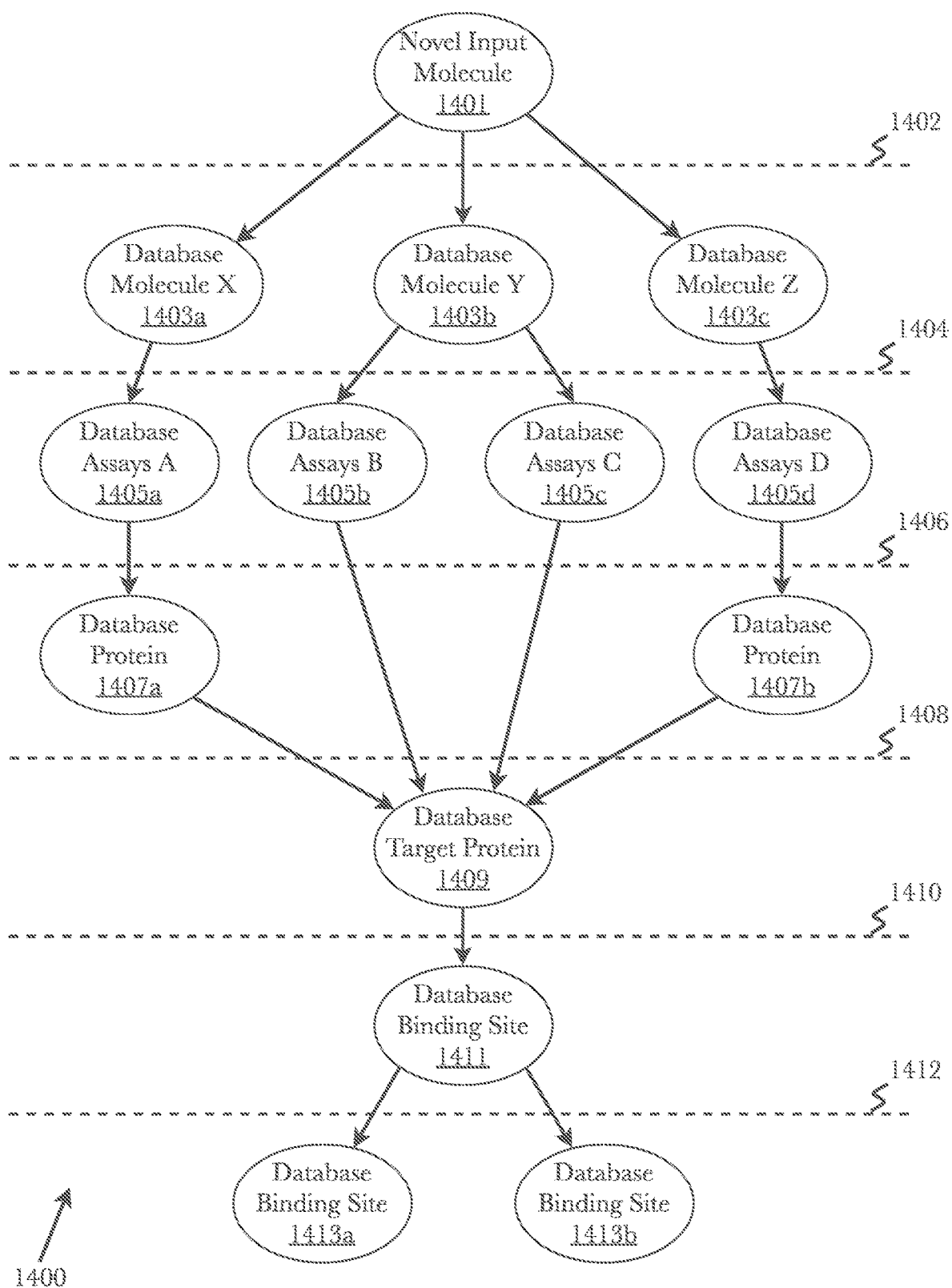
FIG. 14 is a flow diagram illustrating an exemplary similarity search process wherein the input query is a novel molecule, according to an embodiment.

FIG. 14 is a flow diagram illustrating an exemplary similarity search process 1400 wherein the input query is a novel molecule, according to an embodiment. Knowledge graph 215 may be used to conduct vertical and horizontal searching via the EDA interface 230. Vertical searching of the knowledge graph finds a target search term and retrieves a specific subset of related information, for example, a molecule is searched and related assay information is retrieved. Horizontal searching of the knowledge graph uses similarity search functions to retrieve information about similar search terms, for example, a molecule is searched and the similarity search functions return similar, related molecules. A common use case for the automated pharmaceutical research system achievable with knowledge graph 215 and EDA 230 tool is to conduct a similarity search for a novel molecule. The process begins when EDA 230 is accessed and a novel molecule is input 1401 into a search bar. The novel molecule may be input as a string in the form of a chemical formula (e.g., $C_2H_4O_2$), using SMILES convention, or using FASTA convention. In another embodiment, the novel molecule may be input as a structural formula. The input molecule undergoes a fingerprint similarity search 1402 that identifies existing related molecules, stored within the knowledge graph of the data platform 110, that have similar molecular fingerprints.

Molecular fingerprints are a way of encoding the structural and chemical information of a molecule. The most common type of fingerprint is a series of binary bits that represent the presence or absence of particular substructures in the molecule. Fingerprint similarity search 1402 may be conducted using a plurality of similarity metrics known in the art such as Tanimoto, Dice, Cosine, Substructure and Superstructure similarities, and definitions derived from Manhattan, Euclidean, and Soergel distances. In one embodiment, a combination of similarity metrics may be calculated and combined to form an aggregate similarity score wherein if the aggregated score meets a pre-determined threshold the molecules may be considered similar. In a preferred embodiment, a multithreaded Tanimoto search, written in the C computer programming language to optimize the speed of the search, may be implemented to conduct fingerprint similarity search 1402 between query molecules and database molecules. The Tanimoto search compares fingerprints and the similarity is computed using the Jaccard index which is used to quantify the similarity of two sample sets (i.e. two binary fingerprint strings). The Jaccard index produces a number value between zero and one, wherein a Jaccard value of one indicates that the two fingerprints are exactly similar. A multithreaded approach further increases the speed of the fingerprint search by facilitating parallel processing of Tanimoto search routines. Molecule fingerprint data may be preprocessed into a binary pickle string and stored in a binary pickle file to enable rapid parsing and comparison via the multithreaded Tanimoto search.

All similar, related database molecules 1403a-c are retrieved from knowledge graph 215, in this case there were three database molecules identified as similar to the input molecule. For each database molecule identified as similar to the input molecule, all related assays linked to each retrieved database molecule 1403a-c are retrieved 1404 from knowledge graph 215. For instance, database molecule X 1403a was identified as similar to input molecule 1401 and retrieved, then all database assays 1405a related to molecule X 1403 are retrieved. Each database assay 1405a-d may convey information about the relationship between a database molecule 1403a-c and a database protein 1407a-b. The related database protein for each database assay is retrieved 1406. Database assay A 1405a is related to database protein 1407a and database assay D 1405d is related to a different database protein 1407b. These two database proteins each undergo a protein similarity search 1408 to identify possible protein(s) that may interact with the novel input molecule. In one embodiment, the protein similarity search 1408 may be conducted using a basic local alignment search tool (BLAST) which finds regions of local similarity between biological sequences of retrieved, related database proteins 1407a-b and other biological sequences stored within knowledge graph 215 by measuring the similarity between two FASTA strings, and then calculates the statistical significance of the local similarity. For each database protein its FASTA string data is retrieved and the BLAST tool compares the sequences of all proteins contained within the data platform. The protein similarity search 1408 identifies a database target protein 1409 which may be able to interact with novel input molecule 1401.

Once a target protein 1409 has been identified, all binding sites related to the database target protein 1411 are retrieved 1410. A database binding site 1411 is then input into a binding site similarity search 1412 which identifies similar binding sites 1413a-b stored within knowledge graph 215. All retrieved data is then exported to EDA 230 to provide a system user with a collated and searchable profile of information comprising molecules, assays, proteins, and binding sites that may be related to the novel input molecule 1401. The profile is searchable in that it allows users, for example, to click on an identified database assay and then be provided with all information related to that assay such as the health center where the assay was conducted, the research paper associated with the assay, the molecules or proteins studied via the assay, etc.

For example, a research entity, such as a health or medical research center, academic research institute, or a private research company may develop a novel molecule through a variety of biological or chemical processes. Being a novel molecule, the research entity may need to conduct further research in the form of assays to identify possible use cases and biochemical and biomedical interactions and relationships with existing molecules and proteins. Designing and conducting new assays and experiments can be financially costly and time consuming. As a preliminary step, a research entity may utilize the system for automated pharmaceutical research to conduct a similarity search of its novel molecule that returns a comprehensive profile detailing similar existing molecules, assays associated with the similar molecules, proteins related to the assays, and potential protein binding sites that may be compatible with the novel molecule. The research entity may then use the properties of the identified similar molecules and the associated assays for each identified molecule as a basis for developing its own assays or experiments. Additionally, the identified similar binding sites within the comprehensive profile may indicate potential use cases for the novel molecule.

Figure 15:
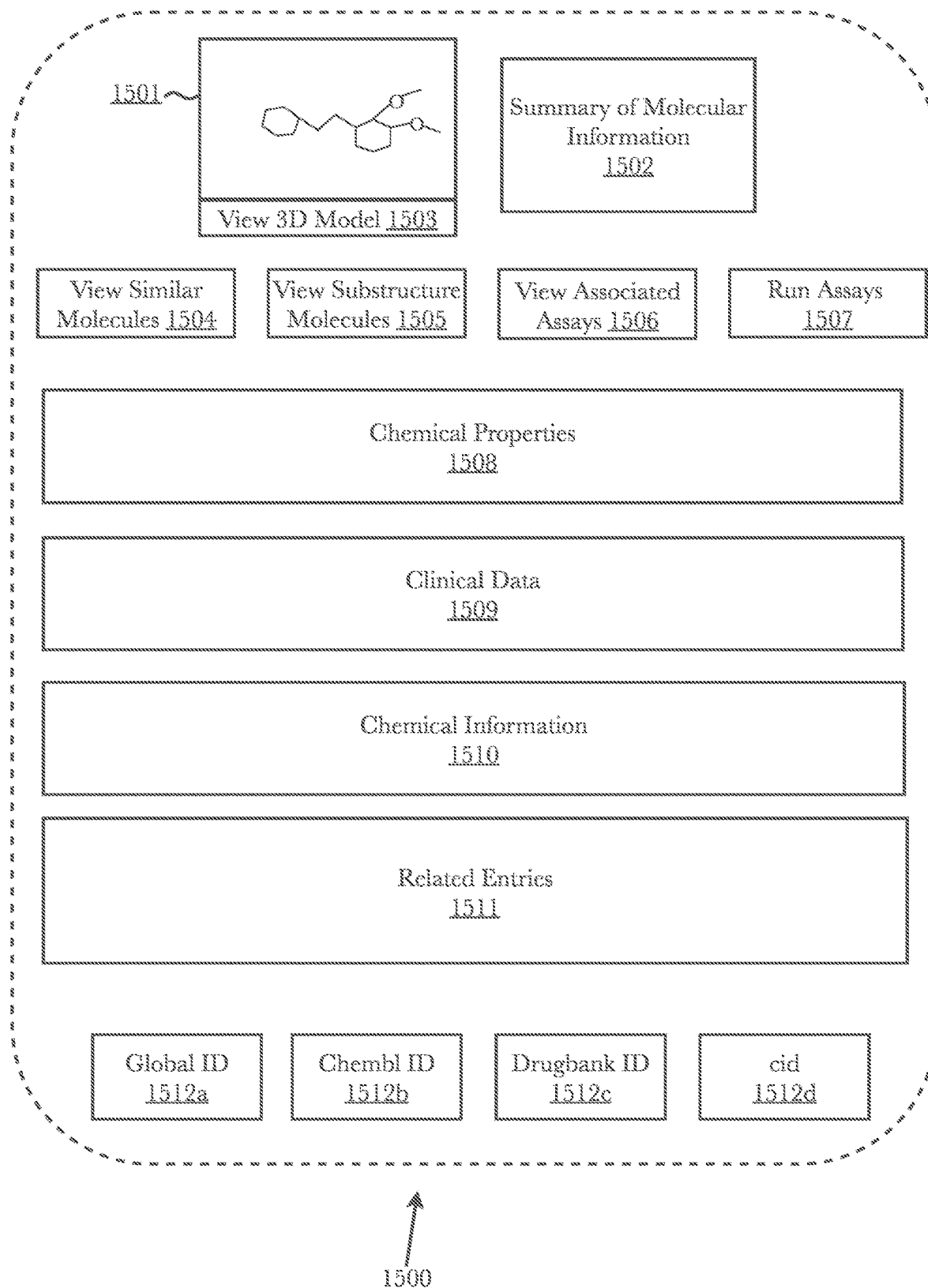
FIG. 15 is a diagram illustrating an exemplary search result page produced using an EDA interface to search for a given molecule, according to an embodiment.

FIG. 15 is a diagram illustrating an exemplary search result page 1500 produced using an EDA interface 230 to search for a given molecule, according to an embodiment. A user may access EDA interface 230 and type the name of a molecule into a search bar. EDA 230 queries knowledge graph 215 for all available data related to the queried molecule and returns the query results on a search result page 1500 fully populated with collated information from a plurality of scraped, parsed, and indexed databases (e.g., Pubchem, ChEMBL, Drugbank, etc.) as well as extracted literature information from available data sources (e.g., abstracts, clinical trial reports, research papers, etc.) with links 1512a-d and citations to the original material accessible at the bottom of the page. In the use case of a novel input molecule, the search result page 1500 is automatically generated with all possible calculable properties.

At the top of the search result page 1500 the two-dimensional (2D) representation of the molecular structure 1501 of the queried molecule is displayed. Beneath the 2D model 1501 is a button 1503 that allows the molecule to be viewed as a 3D model instead of the 2D representation. Displayed next to the 2D model at the top of the page is a summary of the molecular information 1502 specific to the queried molecule which may contain information such as molecular weight, molecular formula, rule of five violations, heavy atom count, hydrogen bond donor, synthesizability, polar surface area, hydrogen bond acceptor, and aromatic ring count. Below the model structure and the summary of molecular information 1502 are a various functions, such as viewing similar molecules or viewing associated assays, that EDA interface 230 may facilitate on the queried molecule. Selecting one of the function boxes causes EDA 230 to automatically execute the function. One function of EDA 230 is a molecule similarity search 1504 which allows a system user to view similar molecules identified by fingerprint similarity or by molecular substructure similarity. Another possible function of EDA 230 is to allow the user to view the substructure molecules 1505 that comprise the queried molecule. This function will populate a new search result page with collated information related to the substructure molecules. Another function of EDA 230 allows users to quickly search and view all associated assays 1506 related to the queried molecule. An example of a search result page produced using the associated assays function 1506 is provided in FIG. 16. The run assays function 1507 allows the user to simulate the assay experiments related to the queried molecule.

Below the selectable functions is more information related to the queried molecule. Information may be displayed about the chemical properties 1508 of the queried molecule. The chemical property information may include, but is not limited to synthesizability, polar surface area, 3D volume, feature ring count, structural type, quantum electrodynamics, complexity rating, atom information, solubility, and acid dissociation. Additionally, clinical data 1509 related to the queried molecule is displayed and may include information describing the type of clinical data available (e.g., investigational, nutraceutical, experimental, illicit, etc.), and approval and phase status. Chemical information 1510 displayed may include biotech kind, chemical name, chemical scaffold, molecular formula, and the international chemical identifier (InChI) and its associated InChI key which are used to encode and decode molecular information stored in knowledge graph 215. Also located on the search result page is a list of database IDs of other related entries 1511 in knowledge graph 215, such as related proteins and related assays, to name a few. At the very bottom of the search result page 1500 are links 1512a-d to the original source material accessible by selecting a one of the provided IDs. For example, selecting the ChEMBL ID 1512b will retrieve from knowledge graph 215 all information, scraped and ingested from the ChEMBL database, related to the ChEMBL ID 1512b. Likewise, selecting the Drugbank ID 1512c or CID (PubChem database ID) 1512d will return from knowledge graph 215 all available information related to the selected ID. Selecting global ID 1512a will return all data related to the queried molecule from each ingested database collated into knowledge graph 215. This allows the user to view data that was sourced from the preferred database of his or her choosing.

Figure 16:
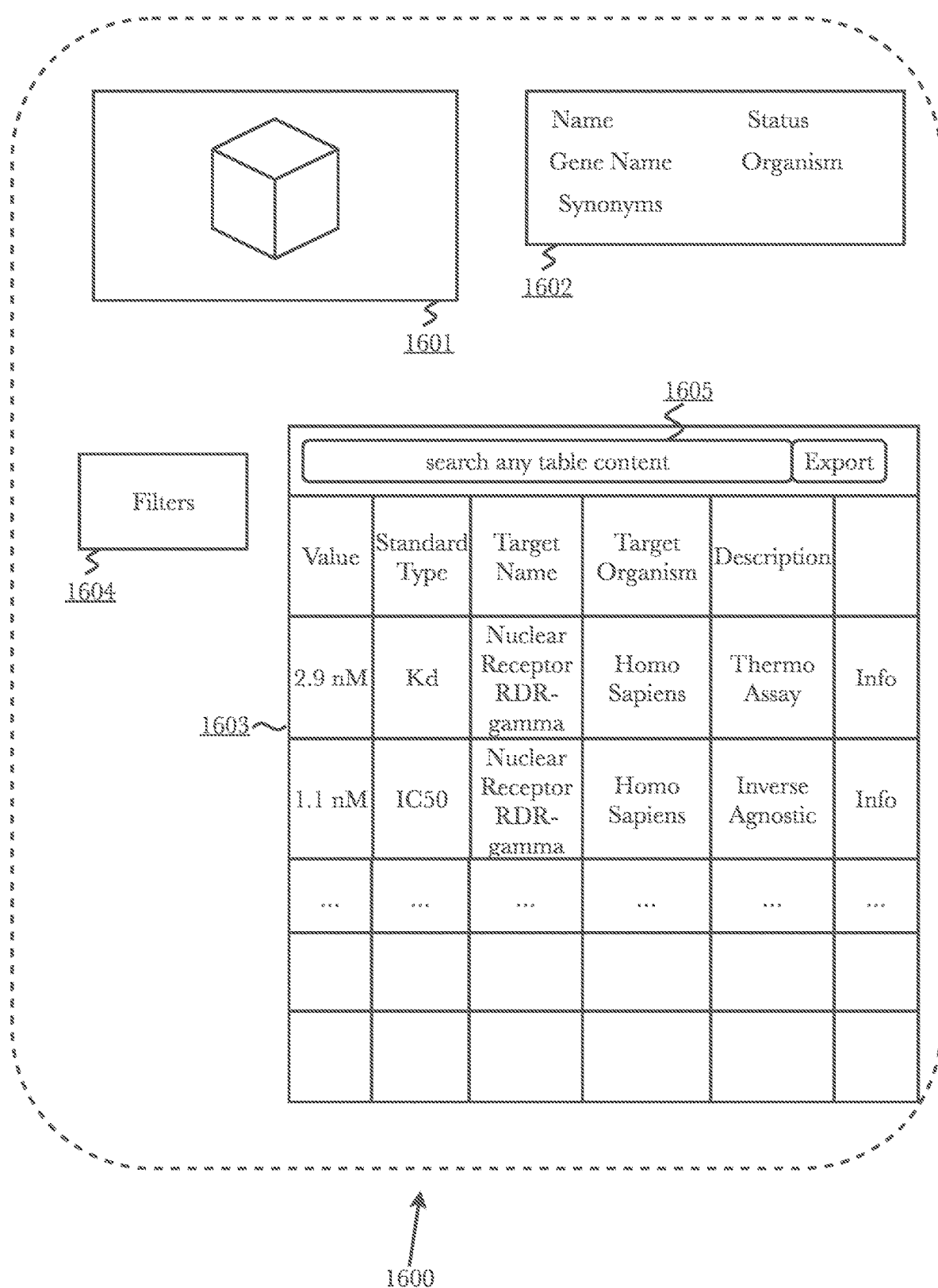
FIG. 16 is a diagram illustrating an exemplary search result page produced using an EDA interface to search for related assays to a given protein, according to an embodiment.

FIG. 16 is diagram illustrating an exemplary search result page 1600 produced using an EDA interface to search for related assays to a given protein, according to an embodiment. A search protein is input into EDA 230 which queries the knowledge graph 215 for all assays related to a search protein and then returns a search result page 1600 displaying the retrieved related assays. At the top of the search result page is a summary of the protein information 1602 including available three dimensional (3D) structure information 1601. The summary of the protein information 1602 may include, but is not limited to the protein name, the genetic name of the protein, the status of the protein (i.e., whether the protein has been peer reviewed or not), and commonly used protein name synonyms. The 3D protein structure 1601 may be interacted with to be viewed from various different angles, and may allow the user to explore the constituent molecules that comprise the searched protein. Below the summary information 1602 and the 3D structure 1601 the related assays 1603 are shown in a table format displaying useful, relevant information about each assay. For instance, the relevant information may contain the quantitative value that was the result of the assay, the standard type of assay that was performed (e.g., inhibitory concentration (IC50), affinity constant (Kd), EC50, etc.), the target receptor studied in assay, the target organism, and a description of the assay. In an embodiment, the target name column contains clickable links that will conduct a search of the clicked, linked target name and return a new search page containing all information related to the target name. Similarly, the description column may contain clickable links that will retrieve all related information, including extracted literature such as abstracts, full research papers, etc., and return a new search page with the collated information. Additionally, a search bar 1605 may be used to search any content included in the related assays table. In another embodiment, the related assays and their relevant information are displayed in thumbnail format instead of table format. A plurality of filters 1604 may be applied to the related assays to allow for more refined and granular search capabilities. For example, available filters may include, but are not limited to chemical property filters, categorical filters such as standard type, target name, target organism, database reference code, etc., geolocational filters, and methodological filters. Search result page 1600 return a comprehensive list of assays related to the queried protein.

Figure 19:
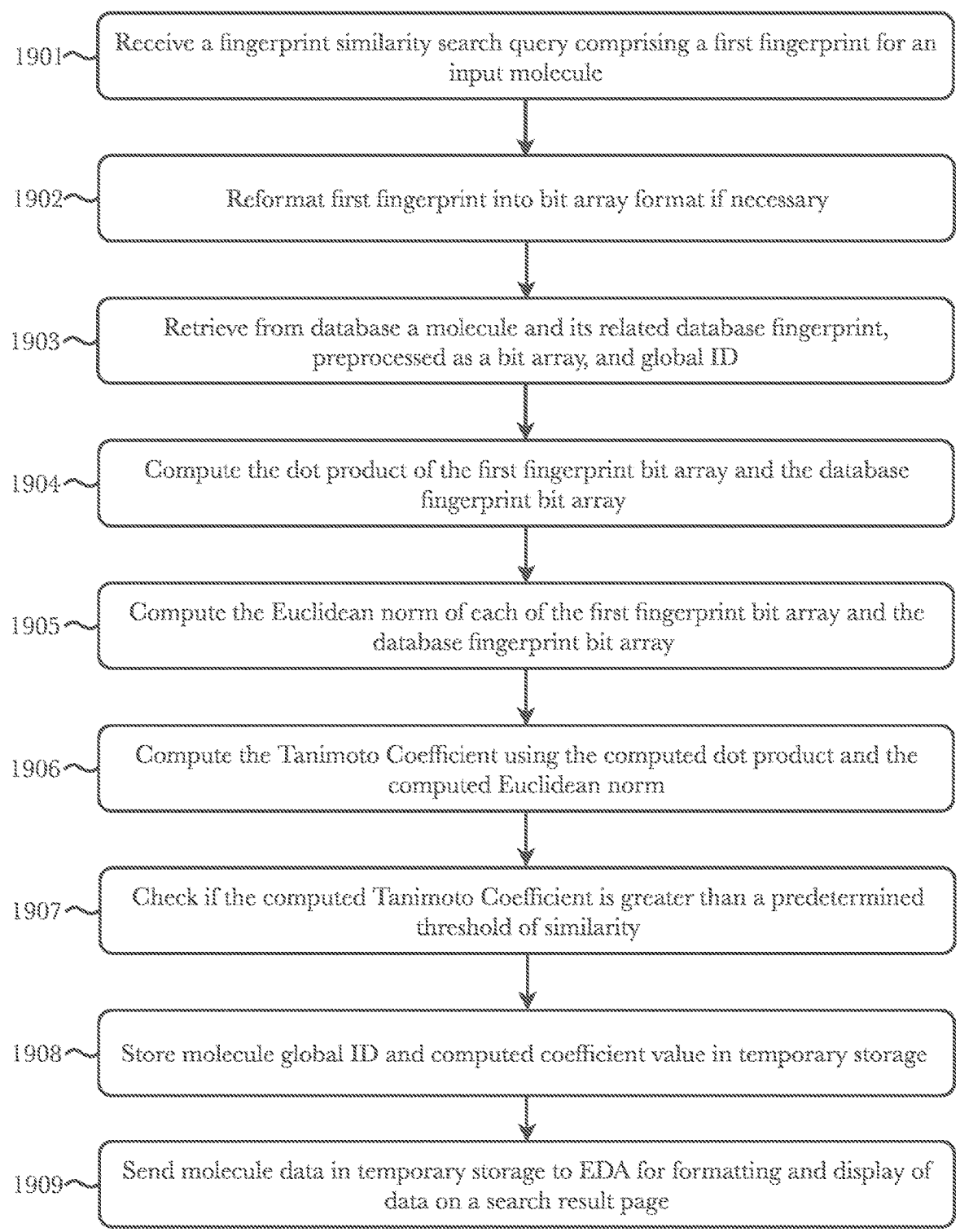
FIG. 19 is a flow diagram illustrating an exemplary method for fingerprint similarity search, according to an embodiment.

FIG. 19 is a flow diagram illustrating an exemplary method 1900 for fingerprint similarity search, according to an embodiment. A fingerprint similarity search begins when the data platform 110 receives a fingerprint similarity search query 1901 comprising the fingerprint (first fingerprint) data for an input molecule. When molecule data is first ingested into the data platform its associated fingerprint data, usually in SMILES format, may be pre-processed into a binary string and stored as a bit array (vector) in the molecule database. This pre-processing step is necessary to optimize the run time of the similarity search routine. If the fingerprint data for the input molecule is not in a binary string format, then it is quickly transformed into a bit array 1902. Next, data platform 110 may retrieve from the molecule database, a molecule and its related database fingerprint and assigned global ID 1903. The dot product between the first fingerprint bit array and the database fingerprint bit array 1904. The next step 1905 computes the Euclidean norm for each of the first fingerprint and database fingerprint. These two computed values are then used as inputs to compute the Tanimoto Coefficient 1906 of the two fingerprints. The Tanimoto Coefficient is a numerical value between 0 and 1, where zero indicates no similarity and one indicates the pair are identical. If the computed Tanimoto Coefficient value is greater than a predetermined threshold of similarity 1907, then store the database molecule's global ID and its computed coefficient value in temporary storage 1908. If the computed coefficient value is not greater than the threshold, then the next molecule in the molecule database is retrieved and steps 1903-1907 may be performed again. This process may be repeated a plurality of times iterating through a subset of the molecule database until all data entries within the subset have been compared for similarity. When that occurs, the data platform 110 forwards all identified molecules contained in the temporary storage to the EDA 230 where it may be displayed on a search result page 1909.

Figure 21:
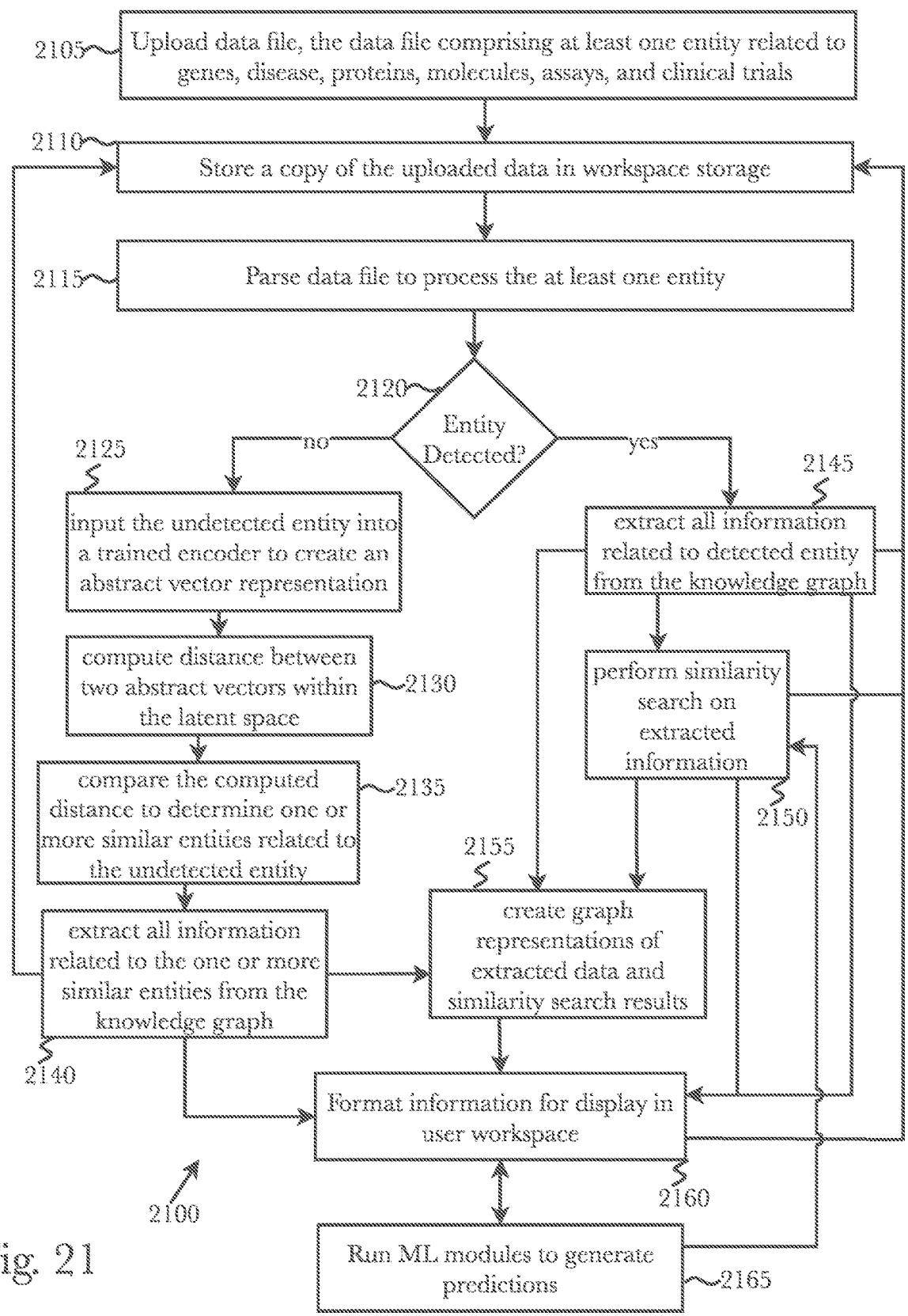
FIG. 21 is a flow diagram illustrating an exemplary method for processing and analyzing uploaded data files, according to an embodiment.

FIG. 21 is a flow diagram illustrating an exemplary method 2100 for processing and analyzing uploaded data files, according to an embodiment. A pharmaceutical or biomedical researcher may create a research workspace in order to gather and store information and context data related to his or her current area of research. According to an embodiment, the process begins when a researcher uploads a data file 2105, the data file comprising at least one biochemical or biomedical entity which may be related to genes, disease, proteins, molecules, assays, and clinical trials. A copy of the uploaded data file may be created and then stored 2110 in a workspace storage for future use. The copy of the uploaded data file may be logically linked to the researcher's workspace such that loading a workspace from workspace storage also retrieves any previously uploaded data files. Next, the uploaded data file is parsed 2115 in order to identify single biochemical or biomedical entities within a possible plurality of biochemical or biomedical entities contained in the uploaded data file. For example, an uploaded data file is a CSV file which contains a plurality of FASTA sequences, and this CSV is parsed such that each line containing a FASTA sequence may be processed as a single biochemical or biomedical entity. A next step may involve analyzing a parsed biochemical or biomedical entity to detect if it already exists within the system database and knowledge graph, or if it is a novel entity 2120. If the parsed biochemical or biomedical entity is an undetected (e.g., novel) entity then it may be fed 2125 as input into a trained encoder to create an abstract vector representation of the undetected biochemical or biomedical entity. Next, the distance between two abstract vectors (one of which is the created abstract vector for the undetected biochemical entity) within the latent space is computed 2130 and compared 2135 against a threshold to determine one or more similar biochemical or biomedical entities related to the undetected biochemical or biomedical entity. The next step is to extract all information related to the one or more similar entities from the knowledge graph 2140 and then send the extracted information to a workspace manager 2019 where it may be formatted for display in the researcher's workspace 2160.

If parsed biochemical or biomedical entities are detected as already existing within the system database and knowledge graph, then the next step is to extract all information related to the detected biochemical or biomedical entity from the knowledge graph 2145. The extracted information may be sent for formatting for display in a researcher's workspace 2160 and used to perform similarity search on extracted information 2150. Extracted information and the results of similarity searches may be used to create graph representations of extracted data and similarity search results 2155. Extracted information for both detected and undetected biochemical entities, created graph representations, and the results of similarity searches may be formatted for display in a researcher's workspace 2160. Furthermore, after an uploaded data file has been completely parsed and processed, a researcher, as a final step, can run one or machine and deep learning modules using uploaded or extracted data to generate predictions 2165, such as predictions about a biochemical or biomedical entity's Bioactivity levels. Output from the ML modules 2165 may be feedback into the similarity search system 2150 and entity detection systems. In this way, new knowledge and predictions generated by the ML modules can be used to detect entities and perform similarity searches on.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 22:
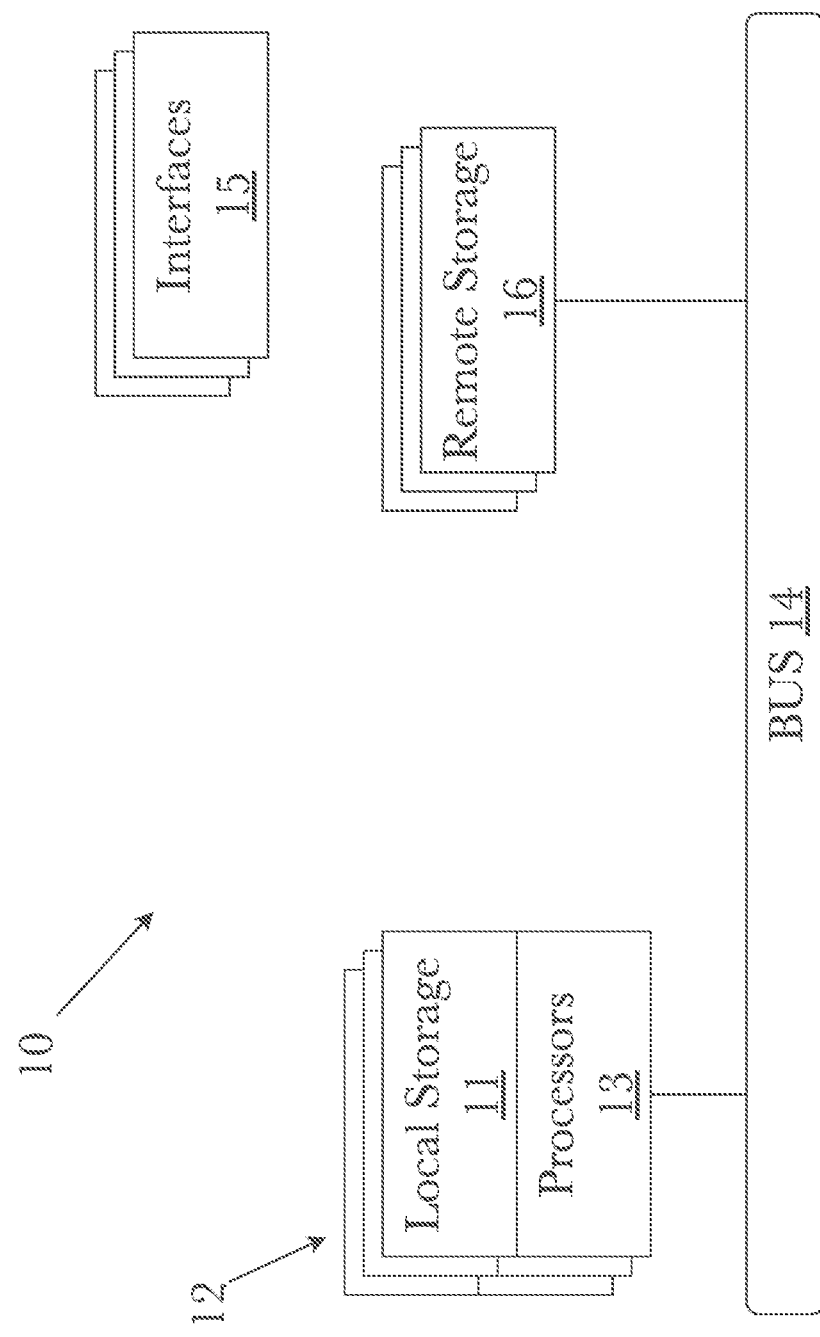
FIG. 22 is a block diagram illustrating an exemplary hardware architecture of a computing device.

Referring now to FIG. 22, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/N hardware interfaces) and, in some instances, volatile and/or non-volatile memory (e.g., RAM).

Although the system shown in FIG. 22 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 23:
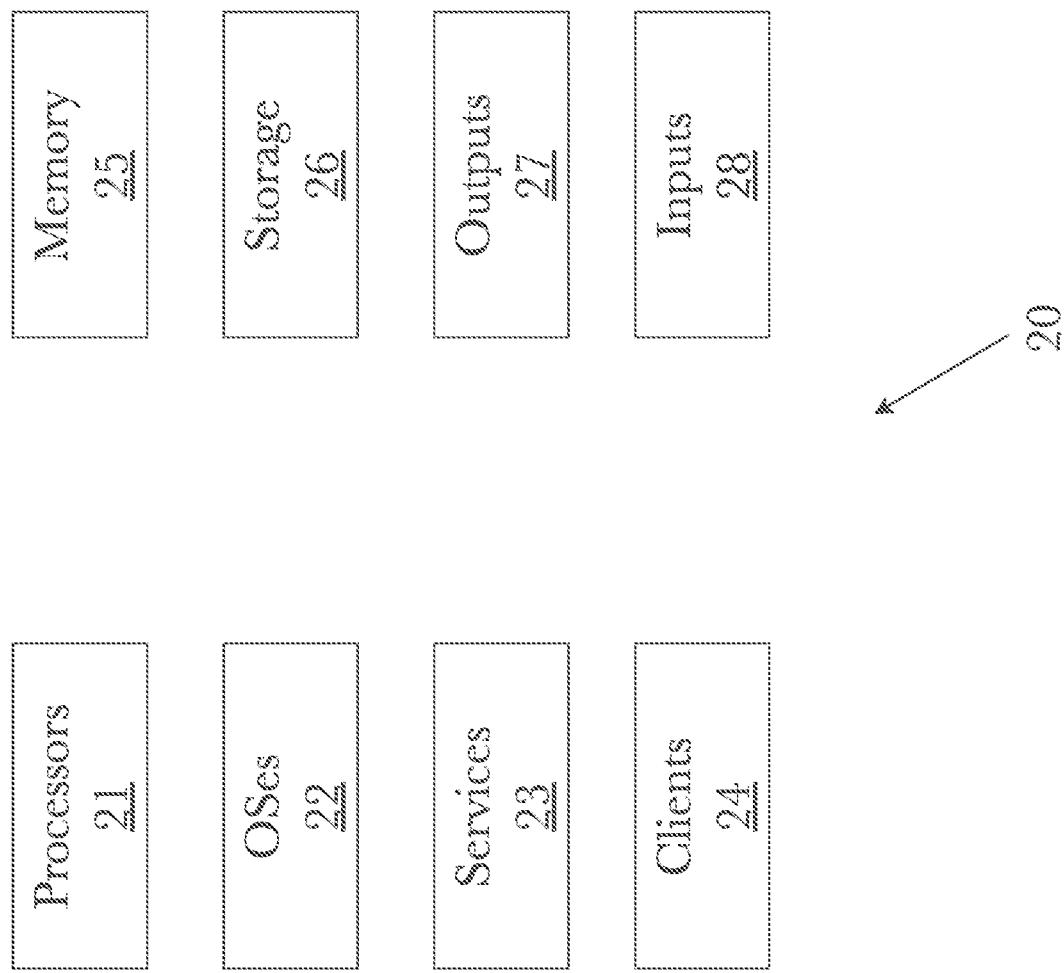
FIG. 23 is a block diagram illustrating an exemplary logical architecture for a client device.

In some aspects, systems may be implemented on a standalone computing system. Referring now to FIG. 23, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 22). Examples of storage devices 26 include flash memory, magnetic hard drive, CD-ROM, and/or the like.

Figure 24:
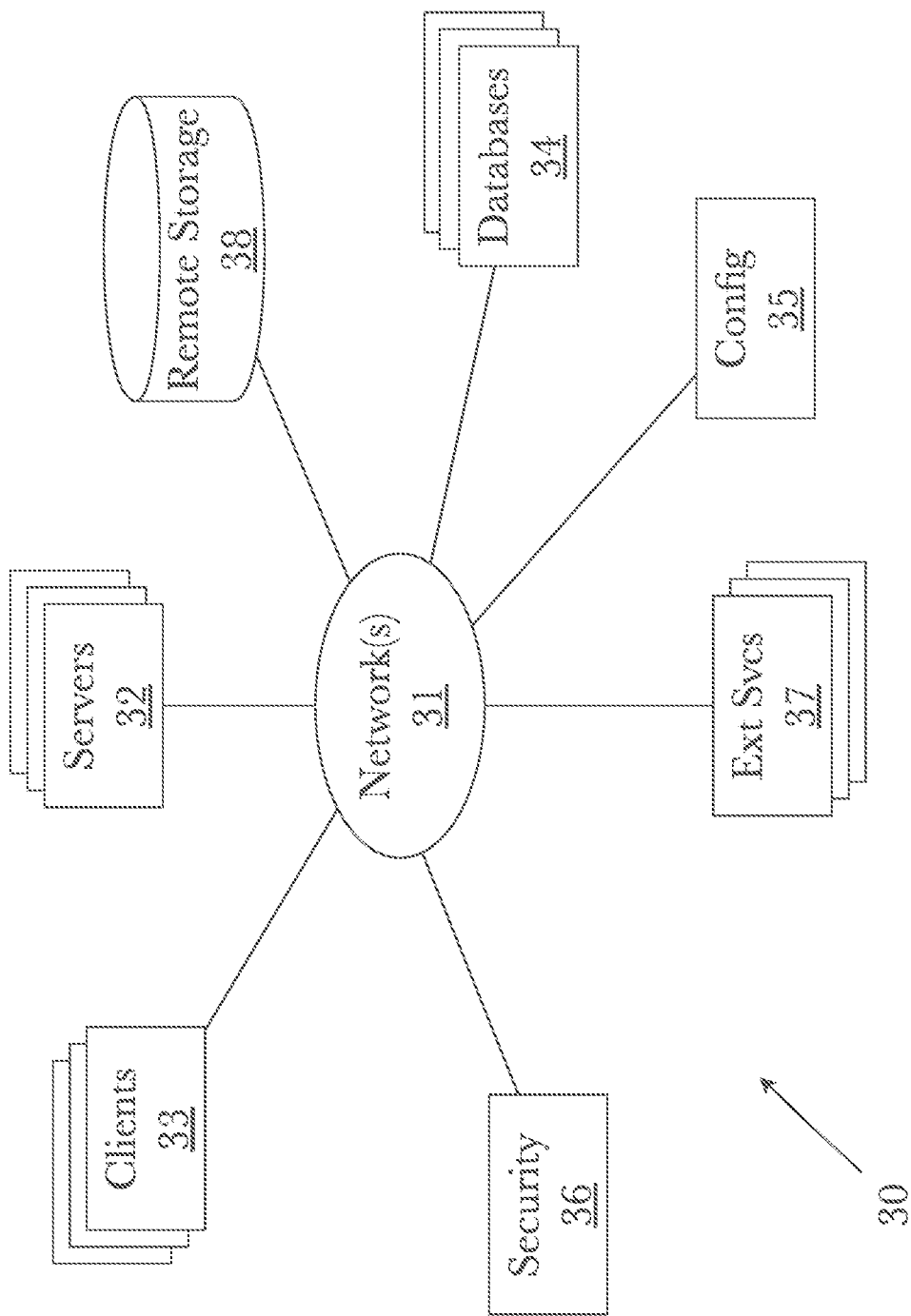
FIG. 24 is a block diagram showing an exemplary architectural arrangement of clients, servers, and external services.

In some aspects, systems may be implemented on a distributed computing network, such as one having any number of clients and/or servers. Referring now to FIG. 24, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 23. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 25:
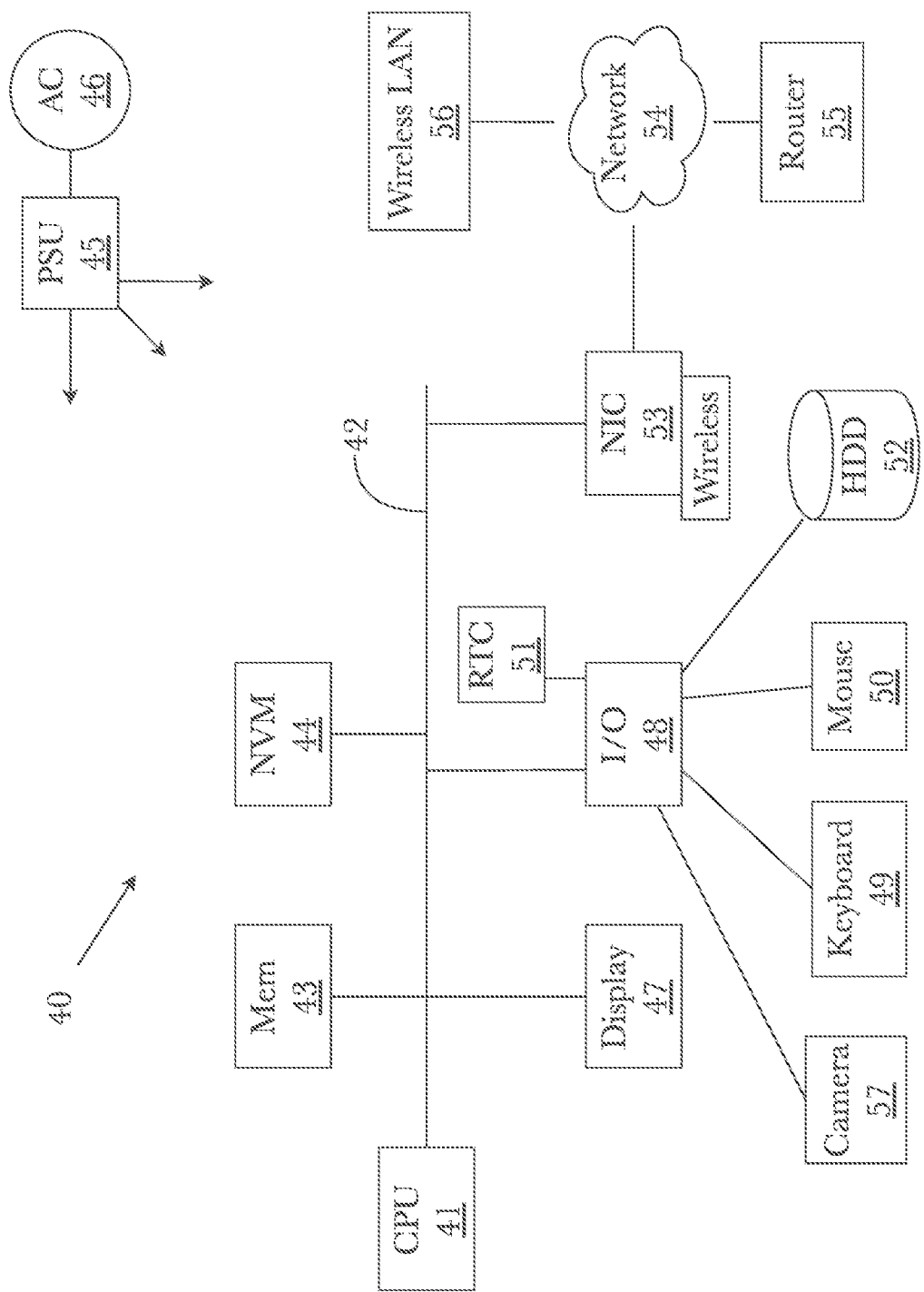
FIG. 25 is another block diagram illustrating an exemplary hardware architecture of a computing device.

FIG. 25 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A system for automated pharmaceutical research utilizing context workspaces, comprising:
  a computer system comprising a memory and a processor;
  a workspace database, comprising information related to uploaded biochemical and biomedical data files, extracted information, and saved workspace data;
  a biochemical database, comprising biochemical and biomedical information related to at least, genes, disease, proteins, molecules, drugs, clinical trials, assays, and biological pathways/mechanisms;
  a workspace drive engine, comprising a first plurality of programming instructions stored in the memory of, and operating on the processor, wherein the first plurality of

41 programming instructions, when operating on the processor, cause the computer system to:
create a new workspace;
store the created workspace in the workspace database;
receive an uploaded data file, the uploaded data file comprising at least one biochemical or biomedical entity;
create a copy of the uploaded data file;
store the copy of the uploaded data file in the workspace database;
parse the uploaded data file into individual biochemical or biomedical entities;
determine if the individual biochemical or biomedical entity exists within the biochemical database, wherein a detected biochemical or biomedical entity indicates the individual biochemical or biomedical entity exists in the biochemical database, and an undetected biochemical or biomedical entity indicates the individual biochemical or biomedical entity does not exist in the biochemical database;
send an undetected biochemical or biomedical entity to a data analysis engine;
extract all information related to a detected biochemical or biomedical entity from a knowledge graph;
create a graph-based representation of the extracted information;
receive data related to a decoded vector from a data analysis engine;
extract all information related to the decoded vector from the knowledge graph; and
format the data related to the decoded vector, the extracted information, and the graph-based representation for display in the workspace; and
a data analysis engine, comprising a second plurality of programming instructions stored in the memory of, and operating on the processor, wherein the second plurality of programming instructions, when operating on the processor, cause the computer system to:
receive the undetected biochemical or biomedical entity;
input the undetected biochemical or biomedical entity into a trained encoder to create an abstract vector representation of the undetected biochemical or biomedical entity, existing in the abstract latent space of a three-dimensional convolutional neural network;
compute the distance between two abstract vectors within the latent space;
compare the computed distance to a predetermined threshold of similarity, wherein a computed distance less than the threshold indicates non-similarity between the two abstract vectors and a computed distance greater than the threshold indicates similarity; and
decode the abstract vector that is greater than the threshold and return to the workspace drive engine data related to the decoded vector as a response to the received undetected biochemical or biomedical entity.

2. The system of claim 1, wherein the computer system is a distributed computer system comprising at least one or more processors and at least one or more memories.

3. The system of claim 1, wherein one of the two abstract vectors within the latent space is the abstract vector representation of the undetected biochemical or biomedical entity.

4. The system of claim 1, further comprising a graphic user interface, comprising a third plurality of programming

42 instructions stored in the memory of, and operating on the processor, wherein the third plurality of programming instructions, when operating on the processor, cause the computer system to:
display a workspace; and
transmit workspace search queries to an exploratory drug analysis interface.

5. A method for automated pharmaceutical research utilizing context workspaces, comprising the steps of:
creating a new workspace;
storing the created workspace in the workspace database;
receiving an uploaded data file, the uploaded data file comprising at least one biochemical or biomedical entity;
creating a copy of the uploaded data file;
storing the copy of the uploaded data file in the workspace database;
parsing the uploaded data file into individual biochemical or biomedical entities;
determining if the individual biochemical or biomedical entity exists within the biochemical database, wherein a detected biochemical or biomedical entity indicates the individual biochemical or biomedical entity exists in the biochemical database, and an undetected biochemical or biomedical entity indicates the individual biochemical or biomedical entity does not exist in the biochemical database;
sending an undetected biochemical or biomedical entity to a data analysis engine;
extracting all information related to a detected biochemical or biomedical entity from a knowledge graph;
creating a graph-based representation of the extracted information;
receiving data related to a decoded vector from a data analysis engine;
extracting all information related to the decoded vector from the knowledge graph;
formatting the data related to the decoded vector, the extracted information, and the graph-based representation for display in the workspace;
receive the undetected biochemical or biomedical entity;
inputting the undetected biochemical or biomedical entity into a trained encoder to create an abstract vector representation of the undetected biochemical or biomedical entity, existing in the abstract latent space of a three-dimensional convolutional neural network;
computing the distance between two abstract vectors within the latent space;
comparing the computed distance to a predetermined threshold of similarity, wherein a computed distance less than the threshold indicates non-similarity between the two abstract vectors and a computed distance greater than the threshold indicates similarity; and
decoding the abstract vector that is greater than the threshold and return to the workspace drive engine data related to the decoded vector as a response to the received undetected biochemical entity.

6. The method of claim 5, wherein the computer system is a distributed computer system comprising at least one or more processors and at least one or more memories.

7. The method of claim 5, wherein one of the two abstract vectors within the latent space is the abstract vector representation of the undetected biochemical or biomedical entity.

8. The method of claim 5, further comprising the steps of:
displaying a workspace; and transmitting workspace search queries to an exploratory drug analysis interface.

\* \* \* \* \*